United States Patent
Ye

(10) Patent No.: US 6,441,272 B1
(45) Date of Patent: Aug. 27, 2002

(54) MODIFICATION OF LIGNIN CONTENT AND COMPOSITION IN PLANTS

(75) Inventor: Zheng-Hua Ye, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/453,323

(22) Filed: Dec. 2, 1999

Related U.S. Application Data

(60) Provisional application No. 60/110,676, filed on Dec. 2, 1998.

(51) Int. Cl.[7] .......................... A01H 1/00; C12N 15/82; C12N 15/87

(52) U.S. Cl. .................... 800/278; 800/295; 435/252.3; 435/252.33; 435/320.1; 536/23.2; 536/24.1

(58) Field of Search .......................... 435/252.3, 252.33, 435/320.1; 536/23.2, 24.1; 800/295, 278

(56) References Cited

U.S. PATENT DOCUMENTS

| | | | |
|---|---|---|---|
| 5,451,514 A | 9/1995 | Boudet et al. | 435/172.3 |
| 5,608,148 A | 3/1997 | John | 800/205 |
| 5,728,570 A | * 3/1998 | Matern et al. | 435/252.3 |

FOREIGN PATENT DOCUMENTS

| | | |
|---|---|---|
| EP | 0 271 988 | 6/1988 |
| WO | WO 93/05160 | 3/1993 |
| WO | WO 94/23044 | 10/1994 |
| WO | WO 98/11205 | * 3/1998 |

OTHER PUBLICATIONS

Akin et al., "Characterization of Digestion Residues of Alfalfa and Orchardgrass Leaves by Microscopic, Spectroscopic and Chemical Analysis," *J. Sci. Food Agric.*, 63:339–347 (1993).

Amrhein et al., "Inhibition of lignin formation by L–α–aminooxy–β–phenylpropionic acid, an inhibitor of phenylalanine ammonia–lyase," *Eur. J. Cell Biol.*, 29:139–144 (1983).

Atanassova et al., "Altered lignin composition in transgenic tobacco expressing O–methyltransferase sequences in sense and antisense orientation," *Plant J.*, 8(4):465–477 (1995).

Baucher et al., "Molecular Tools to Study Lignin Biosynthesis in Poplar," *Med. Fac. Landbouww. Univ. Gent*, 62(4a):1403–1411 (1997).

Becker et al., "New plant binary vectors with selectable markers located proximal to the left T–DNA border," *Plant Mol. Biol.*, 10:1195–1197 (1992).

Bevan et al., "Tissue– and cell–specific activity of a phenylalanine ammonia–lyase promoter in transgenic plants," *EMBO J.*, 8(7):1899–1906 (1989).

Boon, "An Introduction to Pyrolysis Mass Spectrometry of Lignocellulosic Materials: Case Studies on Barley Straw, Corn Stem and Agropyron," *Physico–Chemical Characterization of Plant Residues for Industrial and Feed Use*, Chesson et al., eds., Elsevier Applied Science, New York, Title page, publication page, and pp. 25–49 (1989).

Boudet et al., "Tansley Review No. 80: Biochemistry and molecular biology of lignification," *New Phytol.*, 129:203–236 (1995).

Boudet et al., "Lignin genetic engineering," *Molecular Breeding*, 2:25–39 (1996).

Boudet, "A new view of lignification," *Trend in Plant Science*, 3(2);67–71 (1998).

(List continued on next page.)

*Primary Examiner*—Jezia Riley
(74) *Attorney, Agent, or Firm*—Mueting, Raasch & Gebhardt, P.A.

(57) ABSTRACT

Plants and methods of preparing plants having reduced lignin content and/or altered lignin composition are provided. The activities of caffeoyl-CoA O-methyltransferase and/or caffeic acid O-methyltransferase enzymes in the modified plants are reduced.

58 Claims, 18 Drawing Sheets

OTHER PUBLICATIONS

Bradford, "A Rapid and Sensitive Method for the Quantitation of Microgram Quantities of Protein Utilizing the Principle of Protein–Dye Binding," *Anal. Biochem.,* 72:248–254 (1976).

Buxton et al., "Lignin Constituents and Cell–Wall Digestibility of Grass and Legume Stems," *Crop Sci.,* 28(3):553–558 (1988).

Campbell et al., "Variation in Lignin Content and Composition: Mechanisms of Control and Implications for the Genetic Improvement of Plants," *Plant Physiol.,* 110(1):3–13 (1996).

Chapple et al., "An Arabidopsis Mutant Defective in the General Phenylpropanoid Pathway," *Plant Cell,* 4:1413–1424 (1992).

Chiang et al., "Comparison of softwood and hardwood kraft pulping," *Tappi J.,* 71(9):173–176 (1988).

Crowley et al., "Phenocopy of Discoidin I–Minus Mutants by Antisense Transformation in Dictyostelium," *Cell,* 43:633–641 (1985).

Davin et al., "Chapter Eleven: Phenylpropanoid Metabolism: Biosynthesis of Monolignols, Lignans and Neolignans, Lignins and Suberins," *recent advances in phytochemistry, vol. 26: Phenolics Metabolism in Plants,* Stafford et al., eds., Plenum Press, New York, Title page, publication page and pp. 325–375 (1992).

Dean et al., "Biotechnological Modification of Lignin Structure and Composition in Forest Trees," *Holzforschung,* 46(2):135–147 (1992).

Doster et al., "Quantification of Lignin Formation in Almond Bark in Response to Wounding and Infection by Phytophthora Species," *Phytopathology,* 78(4):473–477 (1988).

Douglas, "Phenylpropanoid metabolism and lignin biosynthesis: from weeds to trees," *Trends in Plant Science,* 1(6):171–178 (1996).

Dwivedi et al., "Modification of lignin biosynthesis in transgenic Nicotiana through expression of an antisense O–methyltransferase gene from Populus," *Plant Mol. Biol.,* 26:61–71 (1994).

Elkind et al., "Abnormal plant development and down–regulation of phenylpropanoid biosynthesis in transgenic tobacco containing a heterologous phenylalanine ammonia––lyase gene," *Proc. Natl. Acad. Sci. USA,* 87:9057–9061 (1990).

Harlow et al., *Antibodies: A Laboratory Manual,* Cold Spring Harbor Laboratory, Cold Spring Harbor, New York, Title page, publication page and table of contents, 9 pgs. (1988).

Higuchi, "Chapter 7: Biosynthesis of Lignin," *Biosynthesis and Biodegredation of Wood Components,* Higuchi, ed., Academic Press, Orlando, Title page, publication page and pp. 141–160 (1985).

Horsch et al., "A Simple and General Method for Transferring Genes into Plants," *Science,* 227:1229–1231 (1985).

Iiyama et al., "An improved acetyl bromide procedure for determining lignin in woods and wood pulp," *Wood Sci. Technol.,* 22:271–280 (1998).

Izant et al., "Constitutive and Conditional Suppression of Exogenous and Endogenous Genes by Anti–Sense RNA," *Science,* 229:345–352 (1985).

Jung et al., "Influence of Lignin on Digestibility of Forage Cell Wall Material," *J. Anim. Sci.,* 62(6):1703–1712 (1986).

Kim et al., "Stable Reduction of Thymidine Kinase Activity in Cells Expressing High Levels of Anti–Sense RNA," *Cell,* 42:129–138 (1985).

Kirk et al, "[12] Lignin Determination," *Methods in Enzymology, Volume 161: Biomass, Part B: lignin, Pectin and Chitin,* Wood et al., eds, Academic Press, Inc., Title page and pp. 87–101 (1988).

Kühnl et al., "Elicitor Induced S–Adenosyl–L–Methionine: Caffeoyl–CoA 3–O–Methyltransferase from Carrot Cell Suspension Cultures," *Plant Sci.,* 60:21–25 (1989).

Lee et al., "Antisense Supression of 4–Coumarate: Coenzyme A Ligase Activity in Arabidopsis Leads to Altered Lignin Subunit Composition," *Plant Cell,* 9(11)1985–1998 (1997).

Lewis et al., "Lignin: Occurrence, Biogenesis and Biodegradation," *Ann. Rev. Plant Physiol. Plant Mol. Biol.,* 41:455–496 (1990).

Li et al., "A novel multifunctional O–methyltransferase implicated in a dual methylation pathway associated with lignin biosynthesis in loblolly pine," *Proc. Natl. Acad. Sci. USA,* 94(10):5461–5466 (1997).

Mahert et al., "Increased disease susceptibility of transgenic tobacco plants with suppressed levels of preformed phenylpropanoid products," *Proc. Natl. Acad. Sci USA,* 91:7802–7806 (1994).

Martz et al., "cDNA cloning, substrate specificity and expression study of tobacco caffeoyl–CoA 3–O–methyltransferase, a lignin biosynthetic enzyme," *Plant Mol. Biol.,* 36:427–437 (1998).

Melton, "Injected anti–sense RNAs specifically block messenger RNA translation in vivo," *Proc. Natl. Acad. Sci. USA,* 82:144–148 (1985).

Meyer et al., "Lignin monomer composition is determined by the expression of a cytochrome P450–dependent monooxygenase in Arabidopsus," *Proc. Natl. Acad. Sci. USA,* 95:(12):6619–6623 (1998).

Montgomery et al., "Double–stranded RNA as a mediator in sequence–specific genetic silencing and co–suppression," *Trends in Genetics,* 14(7):255–258 (1998).

Monties, "4: Lignins," *Methods in Plant Biochemistry,* vol. 1: Plant Phenolics, Harborne, eds., Academic Press, Title page and pp. 113–157 (1989).

Morrison et al., "Analysis of Graded Flax Fiber and Yarn by Pyrolysis Mass Spectrometry and Pyrolysis Gas Chromatography Mass Spectrometry," *J. Agric. Food Chem.,* 46(5):1870–1876 (1998).

Negrel et al., "The Phosphohydrolysis of Hydroxycinnamoyl–Coenzyme A Thioesters in Plant Extracts," *Phytochemistry,* 23(1):31–34 (1984).

Neish, "Monomeric Intermediates in the Biosynthesis of Lignin," *Constitution and Biosynthesis of Lignin,* Freudenberg et al., eds., Spring Verlag, New York, Title page, publication page, table of contents and pp. 1–43 (1968).

Ni et al., "Reduced lignin in transgenic plants containing a caffeic acid O–methyltransferase antisense gene," *Transgenic Research* 3:120–126 (1994).

Ni et al., "Stress Responses in Alfalfa," *Plant Physiol.,* 112(2):717–726 (1996).

Pakusch et al., "S–Adenosyl–L–methionine: trans–Caffeoyl coenzyme A 3–O–Methyltransferase from Elicitor–Treated Parsley Cell Suspension Cultures," *Arch. Biochem. Biophys.,* 271(2):488–494 (1989).

Pallas et al., "Tobacco plants epigenetically suppressed in phenylalanine ammonia–lyase expression do not develop systemic acquired resistance in response to infection by tobacco mosaic virus," *Plant J.,* 10(2):281–293 (1996).

Piquemal et al., "Down regulation of Cinnamoyl–CoA Reductase induces significant changes of lignin profiles in transgenic tobacco plants," *Plant J.,* 13(1):71–83 (1998).

Preiss et al., "Molecular genetics of Krüppel, a gene required for segmentation of the Drosophila embryo," *Nature,* 313(5997):27–32 (1985).

Rosenberg et al., "Production of phenocopies by Krüppel antisense RNA injection into Drosophila embryos," *Nature,* 313(6004):703–706 (1985).

Saka et al., "The Distribution of Lignin in White Birch Wood as Determined by Bromination with TEM–EDXA," *Holzforschung,* 42(3):149–153 (1988).

Sambrook et al., *Molecular Cloning: A Laboratory Manual,* Second Edition, Cold Spring Harbor Laboratory Press, Cold Spring Harbor, New York, Title Page, publication page and table of contents only, 30 pgs (1989).

Sederoff et al., "Chapter Twelve: Genetic Regulation of Lignin Biosynthesis and the Potential Modification of Wood in Genetic Engineering in Loblolly Pine," *recent advances in phytochemistry volume 28: Genetic Engineering of Plant Secondary Metabolism,* Ellis et al., eds., Plenum Press, New York, Title page, publication page, and pp. 313–335 (1994).

Sewalt et al., "Reduced Lignin Content and Altered Lignin Composition in Transgenic Tobacco Down–Regulated in Expression of L–Phenylalanine Ammonia–Lyase or Cinnamate 4–Hydroxylase," *Plant Physiol.,* 115(1):41–40 (1997).

Smart et al., "The Influence of Lignification on the Development of Vascular Tissue in *Vigna radiata* L.," *Protoplasma,* 124:87–95 (1985).

Smith et al., "Antisense RNA inhibition of polygalacturonase gene expression in transgenic tomatoes," *Nature,* 334(6184):724–726 (1988).

Smith et al., "Inheritance and effect on ripening of antisense polygalacturonase genes in transgenic tomatoes," *Plant Mol. Biol.,* 14:369–379 (1990).

Tamagnone et al., "The AmMYB308 and AmMYB330 Transcription Factors from Antirrhinum Regulate Phenylpropanoid and Lignin Biosynthesis in Transgenic Tobacco," *Plant Cell,* 10(2):135–154 (1998).

Tsai et al., "Suppression of O–Methyltransferase Gene by Homologous Sense Transgene in Quaking Aspen Causes Red–Brown Wood Phenotypes," *Plant Physiol.,* 117:101–112 (1998).

Van Doorsselaere et al., "A novel lignin in poplar trees with a reduced caffeic acid/5–hydroxyferulic acid O–methyltransferase activity," *Plant J.,* 8(6):855–864 (1995).

Whetten et al., "Genetic engineering of wood," *Forest Ecol. Management* 43:301–316 (1991).

Whetten et al., "Lignin Biosynthesis," *Plant Cell,* 7:1001–1013 (1995).

Ye et al., "An Alternative Methylation Pathway in Lignin Biosynthesis in Zinnia," *Plant Cell,* 6:1427–1439 (1994).

Ye et al., "Differential Expression of Two O–Methyltransferases in Lignin Biosynthesis in *Zinnia elegans,*" *Plant Physiol.,* 108:459–467 (1995).

Ye, "Expression patterns of the cinnamic acid 4–hydroxylase gene during lignification in *Zinnia elegans,*" *Plant Sci.,* 121:133–141 (1996).

Ye, "Association of Caffeoyl Coenzyme A 3–O–Methyltransferase Expression with Lignifying Tissues in Several Dicot Plants," *Plant Physiol.,* 115:1341–1350 (1997).

Zhong et al., "Dual Methylation Pathways in Lignin Biosynthesis," *Plant Cell,* 10(12):2033–2045 (1998).

* cited by examiner

-- The cDNA sequence of tobacco caffeic acid
    O-methyltransferase (CAOMT):

| | | | | |
|---|---|---|---|---|
| GTAAAATGGG | TTCAACAAGC | GAGAGCCAGA | GTAACAGTCT | CACTCACACA | 50
| GAAGACGAAG | CTTTCTTATT | TGCCATGCAA | TTGTGTAGTG | CTTCTGTACT | 100
| TCCTATGGTC | CTAAAATCAG | CCGTAGAACT | TGACCTTCTT | GAGCTAATGG | 150
| CTAAGGCTGG | TCCAGGTGCA | GCTATTTCTC | CTTCTGAATT | AGCTGCTCAG | 200
| CTCTCAACTC | AGAACCCAGA | AGCACCTGTT | ATGCTTGATC | GGATGCTTAG | 250
| GCTACTTGCT | TCTTACTCTG | TTCTCAATTG | TACTCTTAGA | ACACTGCCTG | 300
| ATAGCAGTGT | TGAGAGGCTT | TATAGTCTGG | CTCCCGTCTG | TAAGTACTTG | 350
| ACTAAGAATG | CTGATGGTGT | TTCTGTTGCC | CCACTTTTGC | TTATGAATCA | 400
| AGATAAAGTT | CTTATGGAGA | GCTGGTACCA | CTTAAAAGAT | GCAGTACTAG | 450
| ATGGCGGAAT | CCCATTCAAC | AAAGCCTATG | GAATGACAGC | ATTTGAGTAC | 500
| CATGGCACAG | ATCCAAGATT | CAACAAAGTG | TTCAACCGTG | GAATGTCTGA | 550
| TCACTCCACT | ATGTCAATGA | AGAAGATTCT | TGAGGACTAC | AAAGGATTTG | 600
| AAGGCCTAAA | TTCCATTGTT | GATGTTGGTG | GTGGAACGGG | TGCTACAGTT | 650
| AACATGATTG | TCTCTAAATA | TCCCTCTATT | AAGGGCATTA | ACTTTGATTT | 700
| GCCACATGTA | ATTGGAGATG | CTCCAACTTA | CCCCGGTGTC | GAGCACGTTG | 750
| GTGGCGACAT | GTTTGCTAGT | GTGCCAAAAG | CAGATGCCAT | TTTCATGAAG | 800
| TGGATTTGTC | ATGATTGGAG | CGATGAGCAT | TGCCTAAAAT | TCTTGAAGAA | 850
| TTGCTATGAA | GCACTACCTG | CAAATGGGAA | GGTGATAATT | GCAGAGTGCA | 900
| TACTTCCAGA | GGCCCCAGAT | ACATCACTTG | CAACTAAGAA | TACAGTACAT | 950
| GTTGATATTG | TGATGTTAGC | ACATAACCCA | GGAGGCAAAG | AAAGGACTGA | 1000
| GAAGGAATTT | GAGGCTTTGG | CTAAGGGCGC | TGGTTTTACT | GGTTTCGCAA | 1050
| GGCTTGTTGC | GCTTACAACA | CTTGGGTCAT | GGAATTCAAC | AAGTAATTAA | 1100
| TCGATTCCTT | AATTTGAAGG | ATTAAGCAAT | ATACTGTTCG | TTTTGCATTT | 1150
| GGAAATTCTA | CTTTTCTCAG | AGTGGCTTGA | CTGTGAAAAA | AAAAAAAAAA | 1200
| CGACAGCAAC | GGAATTCCGT | TGCTGTCGAT | CTGCAGCAAG | CTCTCTTTAC | 1250
| GAGTACCCTC | GTCAACCTCA | GTATCGATAT | TAGTTTCCAA | TAAAGGTACT | 1300
| ACCATCACAT | GGGGCTCTGT | TAATTGTTAC | CATCAGAATT | ACGCAGCCTA | 1350
| AAACTTGTGA | TTGTAGTTTG | AGCTGTATTC | CGTGTTATTC | CTCAATTCTC | 1400
| TCCCTAAGCA | AGATATTAGC | AGATGATAAA | AAAAAAAAAA | AAAAAAAAAA | 1450
| AAAAAAAAAA | AAAAAAAAAA | AAAAAAAAAA | AAAAAAAAAA | AAAAAAAAAA | 1500
| AAAAAAA | | | | | 1507

*Fig. 8*

-- The cDNA sequence of tobacco caffeoyl CoA
    O-methyltransferase-1 (CCoAOMT-1):

| | | | | | |
|---|---|---|---|---|---|
| ATGGCAGAGA | ACGGAATTAA | ACACCAAGAG | GTTGGCCACA | AAAGCCTTTT | 50 |
| GCAAAGTGAT | GCTCTTTACC | AGTACATACT | TGAAACCAGT | GTATACCCAA | 100 |
| GAGAGCCAGA | ATCCATGAAA | GAGCTCAGGG | AGGTGACTGC | TAAGCATCCA | 150 |
| TGGAATTTAA | TGACAACATC | AGCGGATGAA | GGGCAGTTTT | TGAACATGTT | 200 |
| GTTGAAGTTG | ATCAATGCCA | AAAACACAAT | GGAGATTGGA | GTTTACACTG | 250 |
| GCTACTCCCT | CCTTGCTACT | GCCCTTGCTA | TCCCCGATGA | TGGAAAGATA | 300 |
| TTGGCAATGG | ACATTAACAG | GGAAAATTAC | GAAATAGGAT | TGCCCATAAT | 350 |
| CGAAAAGGCC | GGTGTGGCTC | ACAAAATTGA | ATTTAGAGAA | GGCCCTGCTT | 400 |
| TGCCCGTTCT | TGATCAACTG | GTTGAAGATA | AAAAGAATCA | TGGCACGTAT | 450 |
| GATTTCATAT | TTGTGGATGC | TGATAAGGAC | AACTACATTA | ACTATCACAA | 500 |
| AAGGATAATA | GATTTGGTGA | AGTTGGTGG | TTTAATTGGG | TACGACAACA | 550 |
| CCCTATGGAA | TGGTTCTGTG | GTGGCTCCAC | CTGATGCACC | AATGAGGAAA | 600 |
| TACGTAAGGT | ATTATAGGGA | CTTCGTGTTG | GAACTTAACA | AAGCCCTAGC | 650 |
| CGTTGATCCA | AGGATTGAGA | TTTGCATGCT | ACCCGTTGGT | GATGGCATTA | 700 |
| CCTTGTGCCG | CCGCATCACC | TGATCATTCC | AATATTCTTT | TGTTTCTTTT | 750 |
| TATTTCTAAA | TATATAAAAT | AAAAAAAACA | TTTTCTTTCT | TTGTTTCTCT | 800 |
| TTTGGTTTAT | AATGTAAGGG | AGGACTTCCT | TTTAAGCTAT | GAGTTTCATA | 850 |
| TTTTTCAAAA | AAAAAAAAA | | | | 870 |

*Fig. 9*

-- The cDNA sequence of tobacco caffeoyl CoA
   O-methyltransferase-2 (CCoAOMT-2):

```
GACGCTCTTT ACCAGTACAT ACTTGAAACC AGTGTATACC CAAGAGAGCC    50
AGAATCCATG AAAGAGCTTA GGGAGGTGAC TGCTAAGCAT CCATGGAATT   100
TAATGACAAC ATCAGCGGAT GAAGGACAGT TCTTGAACAT GTTGTTGAAG   150
TTGATTAATG CTAAAAATAC AATGGAGATT GGAGTTTACA CTGGCTACTC   200
CCTCCTTGCT ACTGCCCTTG CTATCCCCGA TGATGGAAAG ATATTAGCAA   250
TGGACATTAA CAGGGAAAAT TACGAAATAG GATTGCCCAT AATAGAAAAG   300
GCCGGTGTGG CTCACAAAAT TGAATTTAGA GAAGGCCCTG CTTTGCCTGT   350
TCTTGATCAA TTGGTTGAAG ATAAAAGAA TCATGGCACA TATGATTTCA    400
TATTTGTGGA TGCTGACAAG GACAACTACA TTAACTATCA CAAAAGGATA   450
ATAGATTTGG TGAAAGTTGG TGGTTTGATT GGGTACGACA ACACCCTATG   500
GAATGGTTCT GTGGTGGCTC CACCCGATGC ACCAATGAGG AAATACGTAA   550
GGTATTACAG GGACTTTGTA TTGGAGCTTA ACAAAGCCCT AGCCGTTGAT   600
CCTAGGATTG AGATTTGTAT GTTACCTGTT GGTGATGGCA TTACCTTGTG   650
CCGCCGCATC AGCTGATCAT TCCAATATTC TTTTGTTTCT TTTTTATTTC   700
TAAGTATAAA AAAAAAACC TTTTCTTTTT TGTTTCTCTT TTGGTTTATA    750
ATGTAAGGGA GGACTTCCTT TTGAGCTATG AGTATCATAT TATTCAATAA   800
AAAAAAAAA A                                              811
```

*Fig. 10*

-- The cDNA sequence of tobacco caffeoyl CoA
   O-methyltransferase-3 (CCoAOMT-3):

```
GCACAGGAAA ATCAGGTCGC CAAACACCAA GAGGTTGGCC ACAAGAGCCT    50
TTTACAAAGT GATGCTCTTT ACCAGTACAT ACTTGAGACC AGCGTATACC   100
CAAGAGAGCC AGAACCCATG AAAGAGCTCA GAGAATTGAC TGCTAAGCAT   150
CCATGGAATC TAATGACAAC TTCGGCGGAT GAAGGACAAT TCTTGATCAT   200
GCTATTGAAA TTGATCAATG CTAAAAACAC CATGGAAATC GGTGTTTACA   250
CTGGCTACTC CCTCCTTGCT ACTGCTCTTG CTCTTCCCCA TGATGGAAAG   300
ATATTGGCAA TGGATATTAA CAGGGAAAAT TACGAAATCG GGTTGCCCGT   350
AATCCAAAAG CTGGCGTGG CTCACAAGAT TGATTTTCGA GAAGGTCCTG   400
CTTTACCTGT TCTTGATTTA ATGGTTGAAG ATAAAAATAA TCATGGCACG   450
TATGATTTCA TTTTCGTGGA TGCTGACAAG GACAATTACA TCAACTACCA   500
CAAGAGGATA ATAGAATTAG TGAAAGTTGG TGGTGTGATT GGCTACGACA   550
ACACCCTATG GAATGGTTCT GTGGCAGCTC CACCTGATGC CCCTATGAGG   600
AAATACGTAA GGTACTATAG GGATTTCGTA TTGGAACTTA ACAAAGCATT   650
GGCAGCTGAT CCAAGAATTG AGATTTGCAT GCTTCCCGTT GGAGATGGAA   700
TTACCCTGTG CCGCCGCATC AGCTGATTTT TTTTTATCCA ACTACCTTTG   750
TTTTTCTTTT GATTTGTGAA TAAATATTTT GTATCTCATG ACTATTATCG   800
CTATTAATAT TTCTATATAT TTGTATTTCA AAAAAAAAAA AAAAA        845
```

*Fig. 11*

-- The cDNA sequence of tobacco caffeoyl CoA
    O-methyltransferase-9 (CCoAOMT-9):

```
ATGGCTGAGA ACGGTGCAGC ACAGGAAAAT CAGGTTACCA AACACCAAGA    50
GGTTGGCCAC AAGAGCCTTT TGCAAAGTGA TGCTCTTTAC CAGTACATAC   100
TTGAGACCAG CGTATACCCA AGAGAGCCAG AACCCATGAA AGAGCTCAGA   150
GAATTGACTG CTAAGCATCC ATGGAATCTA ATGACAACTT CGGCGGATGA   200
AGGACAATTC TTGAGCATGC TATTGAAGCT GATCAATGCT AAAAATACAA   250
TGGAAATTGG TGTTTACACT GGCTACTCCC TTCTTGCAAC TGCTCTTGCT   300
CTTCCTGATG ATGGAAAGAT ATTGGCAATG GATATTAACA AGGAAAATTA   350
CGAACTCGGG TTGCCCGTAA TCCAAAAGGC TGGCGTGGCT CATAAAATTG   400
ATTTTAGAGA AGGTCCTGCT TTGCCTGTTC TTGATTTAAT GATTGAAGAT   450
AAAAATAATC ATGGCACATA TGATTTCATT TTCGTGGATG CTGACAAGGA   500
CAATTACATC AACTACCACA AGAGAATAAT AGAATTAGTG AAAGTTGGTG   550
GTGTGATTGG CTACGACAAC ACCCTATGGA ATGGTTCTGT GGTGGCTCCA   600
CCTGATGCTC AATGAGGAA ATACGTAAGG TACTATAGGG ACTTCGTATT   650
GGAACTTAAC AAAGCTTTGG CAGCTGATCC AAGAATTGAG ATTTGCATGC   700
TTCCCGTTGG TGATGGAATT ACCCTGTGCC GCCGCATCAG CTGATTTATT   750
CTGTTTATCC AACTACTTTT GTTTTTCTTT TGATTTGTGA ATAAATATTT   800
TGTATCTCAT GATTATCGCT ATTAATATTT CTATATATTT GTATTTCAAA   850
TATTGTACTA CTGAAATTGT AACAAATACT TAAGATTGTA CTACAGAAAT   900
GATTATCGCT CGAGTAAAGT TTATTTACAA AATGATATTT TATCCTTTGT   950
AAAAAAAAAA AAAAAA                                        967
```

*Fig. 12*

-- Sequence alignment of the coding regions of
tobacco CCoAOMT-1 and CCoAOMT-9 cDNAs

```
CCoAOMT-1  ATGGCAGAGAACGG------------AATT---------AAACACCAAGAGGTTGGCCAC
           :::::  :::::::::            ::  :         ::::::::::::::::::::
CCoAOMT-9  ATGGCTGAGAACGGTGCAGCACAGGAAAATCAGGTTACCAAACACCAAGAGGTTGGCCAC

CCoAOMT-1  AAAAGCCTTTTGCAAAGTGATGCTCTTTACCAGTACATACTTGAAACCAGTGTATACCCA
           :: :::::::::::::::::::::::::::::::::::::::::: ::::: ::::::::::
CCoAOMT-9  AAGAGCCTTTTGCAAAGTGATGCTCTTTACCAGTACATACTTGAGACCAGCGTATACCCA

CCoAOMT-1  AGAGAGCCAGAATCCATGAAAGAGCTCAGGGAGGTGACTGCTAAGCATCCATGGAATTTA
           :::::::::::: :::::::::::::::: :: ::::::::::::::::::::::::: ::
CCoAOMT-9  AGAGAGCCAGAACCCATGAAAGAGCTCAGAGAATTGACTGCTAAGCATCCATGGAATCTA

CCoAOMT-1  ATGACAACATCAGCGGATGAAGGGCAGTTTTTGAACATGTTGTTGAAGTTGATCAATGCC
           :::::::: :: :::::::::::: :: ::  :::: ::::  : :::::: ::::::::
CCoAOMT-9  ATGACAACTTCGGCGGATGAAGGACAATTCTTGAGCATGCTATTGAAGCTGATCAATGCT

CCoAOMT-1  AAAAACACAATGGAGATTGGAGTTTACACTGGCTACTCCCTCCTTGCTACTGCCCTTGCT
           ::::: :::::::::: :::: ::::::::::::::::::::  :::::  :::: ::::::
CCoAOMT-9  AAAAATACAATGGAAATTGGTGTTTACACTGGCTACTCCCTTCTTGCAACTGCTCTTGCT

CCoAOMT-1  ATCCCCGATGATGGAAAGATATTGGCAATGGACATTAACAGGGAAAATTACGAAATAGGA
           :  :: ::::::::::::::::::::::::::::: ::::: ::::::::::::::  ::
CCoAOMT-9  CTTCCTGATGATGGAAAGATATTGGCAATGGATATTAACAAGGAAAATTACGAACTCGGG

CCoAOMT-1  TTGCCCATAATCGAAAAGGCCGGTGTGGCTCACAAAATTGAATTTAGAGAAGGCCCTGCT
           ::::::  :::: :::::::: :: ::::::::  ::::::::: :::::::::  ::::::
CCoAOMT-9  TTGCCCGTAATCCAAAAGGCTGGCGTGGCTCATAAAATTGATTTAGAGAAGGTCCTGCT

CCoAOMT-1  TTGCCCGTTCTTGATCAACTGGTTGAAGATAAAAAGAATCATGGCACGTATGATTTCATA
           :::::  :::::::: ::  :: ::::::::::::::::: ::::::::: ::::::::::
CCoAOMT-9  TTGCCTGTTCTTGATTTAATGATTGAAGATAAAAATAATCATGGCACATATGATTTCATT

CCoAOMT-1  TTTGTGGATGCTGATAAGGACAACTACATTAACTATCACAAAAGGATAATAGATTTGGTG
           :: :::::::::::: :::::::: ::::: ::::: ::::: :: ::::::::  :: :::
CCoAOMT-9  TTCGTGGATGCTGACAAGGACAATTACATCAACTACCACAAGAGAATAATAGAATTAGTG

CCoAOMT-1  AAAGTTGGTGGTTTAATTGGGTACGACAACACCCTATGGAATGGTTCTGTGGTGGCTCCA
           ::::::::::::: : :::::  :::::::::::::::::::::::::::::::::::::
CCoAOMT-9  AAAGTTGGTGGTGTGATTGGCTACGACAACACCCTATGGAATGGTTCTGTGGTGGCTCCA

CCoAOMT-1  CCTGATGCACCAATGAGGAAATACGTAAGGTATTATAGGGACTTCGTGTTGGAACTTAAC
           ::::::::  :::::::::::::::::::::: ::::::::::::::: ::::::::::::
CCoAOMT-9  CCTGATGCTCCAATGAGGAAATACGTAAGGTACTATAGGGACTTCGTATTGGAACTTAAC

CCoAOMT-1  AAAGCCCTAGCCGTTGATCCAAGGATTGAGATTTGCATGCTACCCGTTGGTGATGGCATT
           :::::  : ::  : :::::::::::::::::::::::::::  :::::::::::::: :::
CCoAOMT-9  AAAGCTTTGGCAGCTGATCCAAGAATTGAGATTTGCATGCTTCCCGTTGGTGATGGAATT

CCoAOMT-1  ACCTTGTGCCGCCGCATCACCTGA
           :::  ::::::::::::::: ::::
CCoAOMT-9  ACCCTGTGCCGCCGCATCAGCTGA
```

*Fig. 13*

MODIFICATION OF LIGNIN CONTENT AND COMPOSITION IN PLANTS

This application claims the benefit of U.S. Provisional Application No. 60/110,676, filed Dec. 2, 1998.

STATEMENT OF GOVERNMENT RIGHTS

This invention was made with Government support under Contract No. DE-FG02-97ER20258 awarded by the Department of Energy. The Government has certain rights in this invention.

BACKGROUND OF THE INVENTION

Lignin, a complex phenylpropanoid polymer, is the second most abundant natural product after cellulose. In trees, lignin may contribute up to about 20–30% of the dry weight. Lignin is primarily deposited in the cell walls of supporting and conductive tissues, such as fibers and tracheary elements. The mechanical rigidity of lignin strengthens these tissues so that the tracheary elements can endure the negative pressure generated from transpiration without collapse of the tissue. In addition to providing mechanical strength, lignin has significant protective functions. Both the physical toughness and chemical durability of lignin may deter feeding by herbivores. Lignification is a frequent response to infection or wounding, which may provide a physical barrier to block the penetration of pathogens.

However, lignin is undesirable in several aspects. Lignin decreases the digestibility of animal forage crops and must be removed during pulping and paper making, which requires the use of chemicals hazardous to the environment. Lignin also appears to have a negative impact on the utilization of plant and tree biomass. During paper pulping, lignin must be eliminated from wood by chemical treatments that are expensive and polluting. The quantity of lignin in forage crops is also negatively correlated to digestibility and appetence. It has been suggested that even small improvements in the digestibility of forage crops or in the reduction of chemicals used for kraft pulping would be valuable because of the large scale of the industries (Sederoff et al., *Genetic Engineering of Plant Secondary Metabolism*, New York Plenum Press (1994)).

Lignin is derived from the dehydrogenative polymerization of monolignols; notably, p-coumaryl alcohol, coniferyl alcohol and synapyl alcohol. Lignin is heterogeneous in that it is composed of different proportions of these three monolignols in different plant species tissues, cell types and even in the same cell at different developmental stages. For example, gymnosperm lignin is primarily composed of guaiacyl (coniferyl-derived) units, whereas angiosperm dicot lignin is primarily composed of guaiacyl and syringyl (synapyl-derived) units. Grass lignin is typically a mixture of guaiacyl, syringyl and p-hydroxylphenyl (coumaryl-derived) units. At tissue and cell type levels, energy dispersive X-ray analysis has shown that the ratios of guaiacyl to syringyl lignin are 12:88 and 88:12 in fibers and vessels, respectively, of birch wood (Saka et al., *Holzforschung*, 42:149–153 (1988)). Lignin heterogeneity is likely to be controlled by the differential expression of lignin enzymes in different lignified tissues.

Monolignols are synthesized through a phenylpropanoid biosynthetic pathway. The chemical structures of the various monomeric lignin precursors, for example, p-coumaric acid, ferulic acid and sinapic acid, differ typically in the number and position of methoxy groups on the aromatic ring. Thus, the methylation of 3- and/or 5-hydroxyl groups of hydroxycinnamic acids in the biosynthetic pathway is an important step influencing lignin composition. It is well accepted that the methylation pathway is mediated by the enzyme caffeic acid O-methyltransferase (CAOMT). The CAOMT-mediated methylation pathway uses free acids as intermediates.

In 1968, Neish proposed an alternative methoxylation pathway in which the carboxyl group is first activated either on cinnamic acid or on p-coumaric acid, and subsequent hydroxylation and methylation are carried out on these ester forms instead of on the free acids Neish, *Constitution and Biosynthesis of Lignin*, Springer Verlag (1968)). Recently, it was suggested that a methylation pathway mediated by caffeoyl-CoA O-methyltransferase (CCoAOMT) is involved in lignin biosynthesis (Ye et al., *Plant Cell*, 6:1427–1439 (1994)). The association of CCoAOMT with lignification was demonstrated in a number of dicot plants (Ye et al., *Plant Physiol.*, 108:459–467 (1995); Ye, *Plant Physiol.*, 115:1341–1350 (1997)). However, no direct evidence of a role for CCoAOMT in lignification has been identified, and the CCoAOMT-mediated methylation pathway has not been widely accepted due to a lack of genetic evidence supporting such a pathway. A significant reason for the general lack of acceptance of CCoAOMT participation in lignification has been the finding that reduction in CAOMT enzyme activity alone in transgenic plants effectively blocks syringyl lignin production (Atanassova et al., *Plant J.*, 8:465–477 (1995); Van Doorsselaere et al., *Plant Journal*, 8:855–864 (1995); Tsai et al., *Plant Physiol.*, 117:101–112 (1998); Dwivedi et al., *Plant Mol. Biol.*, 26:61–71 (1994)). Thus, doubts have been cast on the role of CCoAOMT in lignin production.

A reduction of lignin content and/or alteration of lignin composition is desirable in that it would reduce the pollution from pulping and improve the digestibility of animal forage. It is therefore of interest to develop methods that allow for the modification of lignin content and/or composition of a particular plant, tree or grass cell and /or tissue for producing plants having reduced lignin content.

SUMMARY OF THE INVENTION

The present invention provides a plant characterized by reduced lignin content and/or altered lignin composition compared to a wild-type plant. Plants of the invention include, for example, gymnosperms, angiosperms or forage crops such as alfalfa, tall fescue and clover. Preferably, the plant is a genetically engineered plant.

Preferably, the plant of the invention exhibits reduced activity of at least one biosynthetic enzyme involved in lignin biosynthesis, compared to the activity of the biosynthetic enzyme in the wild-type plant. In a particularly preferred embodiment, the plant exhibits reduced activity of a caffeoyl-CoA O-methyltransferase enzyme. Optionally, the plant additionally exhibits reduced activity of a caffeic acid O-methyltransferase enzyme compared to the caffeic acid O-methyltransferase enzyme activity of a wild-type plant.

In a preferred embodiment, a plant is genetically engineered in a way that makes use of antisense technology to effect a reduction in the activity of a biosynthetic enzyme. Accordingly, a preferred plant of the invention contains at least one exogenous nucleic acid comprising a nucleotide sequence that is "antisense to" at least a portion of a caffeoyl-CoA O-methyltransferase gene such that when the exogenous nucleic acid is present, the activity of an endogenous caffeoyl-CoA O-methyltransferase enzyme is inhibited. Another preferred plant contains at least two exogenous nucleic acids, a first comprising a nucleotide sequence that is antisense to at least a portion of a caffeoyl-CoA O-methyltransferase gene and a second comprising a nucleotide sequence that is antisense to at least a portion of a caffeic acid O-methyltransferase gene such that when the first and second exogenous nucleic acids are present, the activities of both an endogenous caffeoyl-CoA O-methyltransferase enzyme and an endogenous caffeic acid O-methyltransferase enzyme are inhibited. The exogenous nucleic acids can be present in the plant as part of the same nucleic acid molecule (for example, as when they are present on the same vector); or they can exist as separate molecules (for example, as when they are present on different vectors).

Methods for making the plants of the invention are also provided. Plants are genetically or biochemically engineered to reduce the activity of one or more enzymes involved in the phenylpropanoid biosynthesis pathway of the plant. In one embodiment, the invention provides a method for making a genetically engineered plant that includes transfecting a plant cell with at least one exogenous nucleic acid associated with reduced activity in the plant of at least one biosynthetic enzyme involved in lignin biosynthesis, followed by growing the transfected plant cell into the genetically engineered plant having reduced lignin content compared to the lignin content of a comparable wild-type plant. Preferably, the biosynthetic enzyme is CCoAOMT. In a preferred embodiment, the exogenous nucleic acid includes a nucleotide sequence that is "antisense" to at least a portion of a CCoAOMT gene. Optionally, the plant cell can be additionally transfected with a second exogenous nucleic acid, for example one that is "antisense" to at least a portion of a CAOMT gene. The genetically engineered plant cell is then grown into a plant characterized by reduced lignin content and/or altered lignin composition compared to a wild-type plant.

When antisense technology is used to practice the invention, exogenous nucleic acids are advantageously supplied to the plant cell in the form of one or more expression vectors. Plant cells containing two or more different antisense nucleic acids can be made by transfecting the plant cell with a single vector that encodes all the desired antisense molecules, or by a plurality of vectors, each encoding one or more antisense nucleic acids. Multiple copies of a single antisense nucleic acid can, but need not be included on a single vector. Preferably, each copy of an antisense nucleic acid is operably linked to its own promoter and terminator.

The invention further provides a method for making a genetically engineered plant having altered lignin composition compared to the lignin composition of a comparable wild-type plant. A plant cell is transfected with at least one exogenous nucleic acid associated with altered (i.e., either increased or decreased) activity in the plant of at least one biosynthetic enzyme involved in lignin biosynthesis. The transfected plant cell is then grown into the genetically engineered plant having altered lignin composition.

BRIEF DESCRIPTION OF THE FIGURES

FIG. 8 shows the "sense" cDNA sequence for tobacco caffeic acid O-methyltransferase (CAOMT) (SEQ ID NO: 1).

FIG. 9 shows the "sense" cDNA sequence for tobacco caffeoyl-CoA O-methyltransferase-1 (CCoAOMT1) (SEQ ID NO: 2).

FIG. 10 shows the "sense" cDNA sequence for tobacco caffeoyl-CoA O-methyltransferase-2 (CCoAOMT2) (SEQ ID NO: 3).

FIG. 11 shows the "sense" cDNA sequence for tobacco caffeoyl-CoA O-methyltransferase-3 (CCoAOMT3) (SEQ ID NO: 4).

FIG. 12 shows the "sense" cDNA sequence for tobacco caffeoyl-CoA O-methyltransferase-9 (CCoAOMT9) (SEQ ID NO: 5).

FIG. 13 shows the sequence alignment for the protein coding regions of tobacco CCoAOMT1 (SEQ ID NO: 2) and CCoAOMT9 (SEQ ID NO: 5) cDNAs.

DETAILED DESCRIPTION

Figure 1:
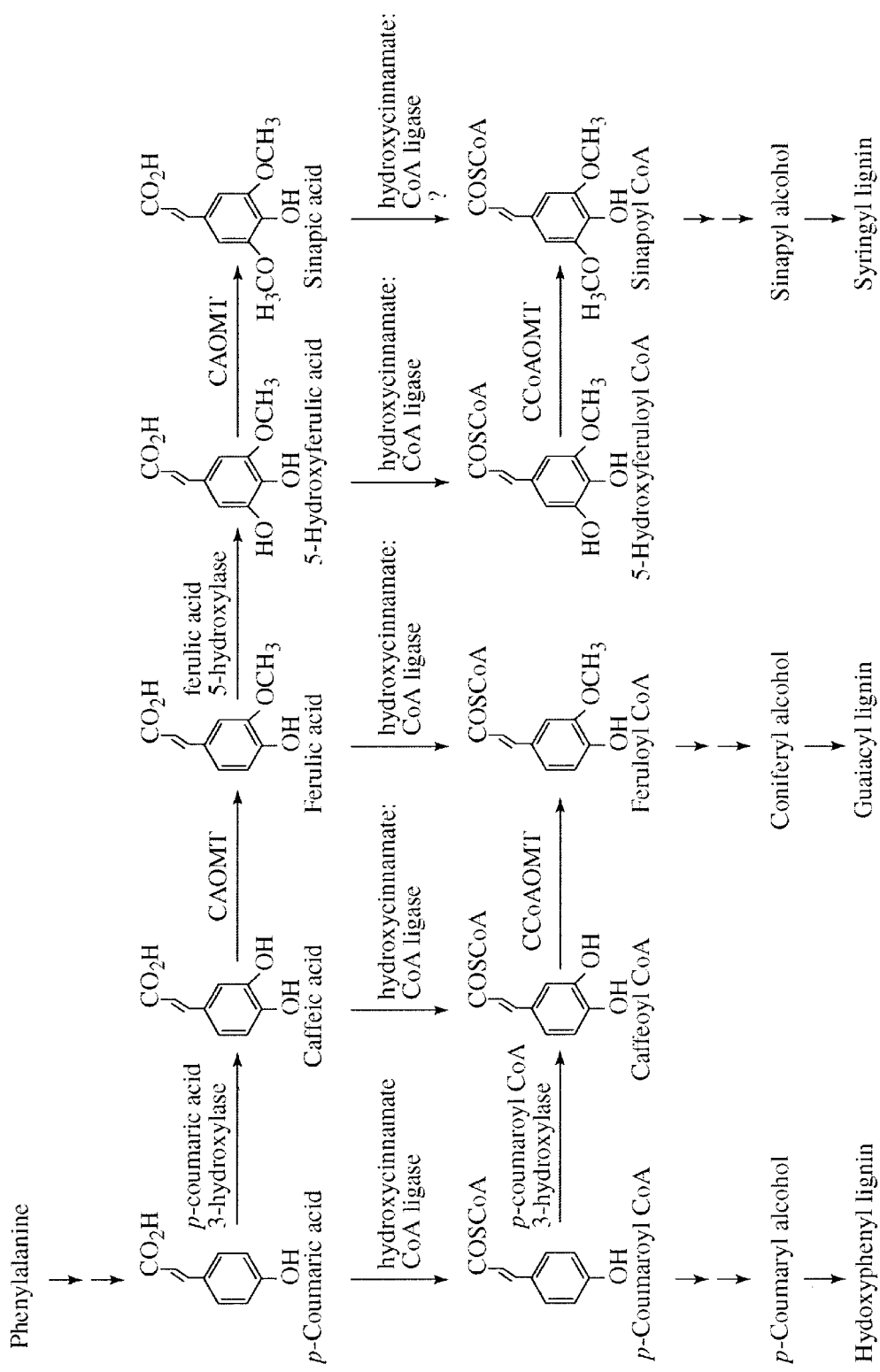
FIG. 1 shows a portion of the phenylpropanoid biosynthesis pathway.

The present invention relates to biotechnological processes for genetic manipulation or genetic alteration of lignin content and/or lignin composition in plants. Important applications of the present invention include, but are not limited to, the improvement of digestibility of forage crops by lignin reduction, reduction of lignin in woody feedstocks for cellulose fibre extraction and improvement of timber quality.

Industrial processes for obtaining cellulosic fibers from woody feedstocks require that lignin first be chemically extracted from the feedstock. Once lignin is removed from the feedstock the cellulosic fibers can be recovered and manufactured into paper or utilized in other ways. For example, the cellulose may be further processed into cellulosic films or yarn for weaving or knitting into fabrics. Reducing the lignin content of plants used as feedstock, typically trees, will lessen the chemical and energy demands of these extractive processes and will also reduce the amount of effluent material, a major potential environmental pollutant that is both difficult and expensive to process. Altering the composition of the lignin in feedstocks is expected to favorably alter the solubility characteristics of the lignin in the chemical extractants used, also leading to reduced usage of chemicals and lower energy requirements.

Typically, monocotyledons utilize all three lignin monomers, e.g., hydroxyphenyl, guaiacyl, and syringyl, for the synthesis of their lignins. Dicotyledons utilize primarily coniferyl and sinapyl alcohols to produce guaiacyl and syringyl lignins, respectively. In contrast, most gymnosperms, e.g., conifers, are mainly composed of guaiacyl lignins. The major difference between angiosperm and gymnosperm lignins is the limited amount of syringyl units in the latter. In general, the efficiency of wood pulping is directly proportional to the amount of syringyl residues in lignin. Thus, altering the lignin composition can increase the efficiency of the wood pulping process.

Alterations in the lignin content or composition of presently unsuitable species may also make alternative feedstocks available to the papermaking and the cut timber industries. Trees characterized by reduced lignin content or having altered lignin composition can lead to a reduction in the cost of the paper as less lignin will have to be removed during the pulping process. Novel papers may be produced due to the purity of cellulose fibre which could otherwise not be obtained.

Plants that can be engineered in accordance with the invention include, without limitation, those that contain lignin. Lignin-containing plants include trees, such as angiosperms, e.g., aspen, sweetgum, yellow poplar (tulip tree), and eucalyptus; gymnosperms, such as conifers, for example, pine; grasses, such as tall fescue; and forage crops, such as alfalfa, maize, lolium, festuca and clover.

It should be understood that the word "plant" is used broadly herein to include any lignin-containing plant material that can be genetically manipulated, including but not limited to, a differentiated or undifferentiated plant cell, a protoplast, a whole plant, a plant tissue, or plant organ, or any component of a plant such as a leaf, stem, root, bud, tuber, fruit, rhizome, or the like.

Lignin monomers are synthesized through the phenylpropanoid biosynthesis pathway (FIG. 1). This pathway is also responsible for the production of a wide range of compounds including flavonoid pigments, isoflavonoids, coumarin phytoalexins and cell division promoting dehydrodiconiferyl glucosides. Briefly, phenylalanine is deaminated to produce p-coumaric acid. p-Coumaric acid is subsequently hydroxylated and methylated, to yield caffeic acid, ferulic acid, 5-hydroxyferulic acid and sinapic acid. The enzyme caffeic acid O-methyltransferase (CAOMT) is known to play a role in this process. By subsequent action on these acid intermediates by a hydroxycinnamate:CoA ligase, p-coumaroyl CoA, caffeoyl-CoA, feruloyl CoA, 5-hydroxyferuloyl CoA and sinapoyl CoA are formed. p-Coumaroyl CoA, feruloyl CoA and sinapoyl CoA are eventually converted to hydroxyphenyl lignin, guaiacyl lignin and syringyl lignin, respectively.

The precise role of caffeoyl-CoA O-methyltransferase (CCoAOMT) in this pathway has been a source of much debate. However, as shown herein by genetic manipulation, endogenous CCoAOMT plays an active role in the phenylpropanoid biosynthesis pathway and appears to be responsible for the methylation of both caffeoyl-CoA and 5-hydroxyferuloyl CoA as shown in FIG. 1. The methylation of caffeoyl-CoA and 5-hydroxyferuloyl CoA by CCoAOMT therefore provides an alternative pathway for lignin biosynthesis. Thus, in a preferred embodiment of the invention, reduction of lignin content and/or alteration of lignin composition in a plant material is achieved by regulating, preferably reducing, the activity of CCoAOMT enzyme. A plant of the invention preferably exhibits reduced levels of CCoAOMT enzyme compared to the level exhibited by a wild-type plant. Optionally, a plant of the invention also has reduced levels of CAOMT activity.

The terms "reduced lignin content" or "decreased lignin content" used herein to describe a plant of the invention refer to a measurable quantitative reduction in the amount of lignin in the plant when compared to the amount of lignin in a comparable control or wild-type plant. A quantitative reduction of lignin is readily ascertained by assays described herein, and by assays known to one of skill in the art, e.g., Klason lignin assay (Kirk et al., *Method in Enzymol.*, 161:87–101 (1988)) or acetyl bromide assay of lignin (Iiyama et al. *Wood Sci. Technol.*, 22:271–280 1988)). A "control" or "wild-type" plant is a plant, such as a native, naturally occurring plant, having a lignin biosynthetic pathway that has not been manipulated in any way.

Reduced lignin content in a plant can be quantitatively measured and described as a percentage of the lignin content found in a comparable wild-type plant. Preferably, lignin content in a plant of the invention is reduced to a level of about 5% to about 90%, more preferably about 10% to about 75%, even more preferably about 15% to about 65% of the lignin content of the wild-type plant. A most preferred embodiment of the plant of the invention has a lignin content of about 20% to about 60% of the wild-type lignin content.

The term "altered lignin composition" as used herein to describe a plant of the invention refers to a measurable quantitative alteration in the relative amounts of hydroxyphenyl, guaiacyl, and syringyl lignin units in the plant compared to a wild-type or control plant. Alteration of the relative amounts of hydroxyphenyl, guaiacyl, and syringyl lignin units is manifested by altered pairwise ratios of the monomers present in the plant when compared to the wild-type plant. Pairwise ratios of any two of the three units can be increased or decreased.

Preferably, a plant having altered lignin composition exhibits a reduced guaiacyl lignin content compared to the guaiacyl lignin content of a comparable wild-type plant; more preferably, it exhibits an increased pairwise syringyl lignin/guaiacyl lignin ratio, i.e., "S/G ratio," compared to the S/G ratio of a comparable wild-type plant. For example, the S/G ratio in a wild-type tobacco plant is typically about 0.70 to about 0.80. The S/G ratio in a tobacco plant that has been genetically engineered according to the invention typically increases to about 0.85 to about 1.10 as guaiacyl lignin is reduced. Thus, depending upon the plant selected for manipulation in the present invention, the S/G ratio of a wild-type plant can be initially established, for example, by a lignin composition assay described herein (Example 5; according to Akin et al., *J. Sci. Food Agric.*, 63:339–347 (1993), and the S/G ratio of a genetically engineered plant, for example, can be compared to that of the wild-type plant. In addition to the advantages to the pulping process conferred by plants with reduced lignin content, plants exhibiting increased S/G ratios provide require fewer chemicals for the kraft pulping process (Chiang et al., Tappi J. 71:173–176 (1988)). A preferred plant of the invention exhibits decreases in both guaiacyl and syringyl lignin units relative to a comparable wild-type plant, while exhibiting an increased S/G ratio. The preceding discussion notwithstanding, however, the S/G ratio in a plant of the invention may be increased or decreased when compared to a wild-type plant.

Reduction of lignin content and/or alteration in lignin composition of a plant material such as a plant, a plant tissue, a plant cell, or the like according to the invention is preferably achieved by regulating the activity of at least one enzyme involved in the lignin biosynthesis pathway, typically through genetically engineering. The activity of these biosynthetic enzymes can be increased or decreased relative to the enzyme activity levels exhibited by or characteristic of a control or wild-type plant. For example, regulation of enzyme activity can be accomplished by increasing or decreasing transcription levels or translation levels, or both, of nucleic acids encoding enzymes involved in lignin biosynthesis, or by similarly regulating the activity of enzymes or cofactors directly or indirectly affecting the activity of those biosynthetic enzymes. The invention is not limited by the technique used to regulate enzyme activity, and any biochemical or genetic technique that can be used to regulate the activity of an enzyme in a cell as described herein is meant to be included in the present invention.

In a preferred embodiment of the invention, reduction of lignin content and/or alteration of lignin composition of a plant is achieved by inhibiting the expression of one or more lignin biosynthetic genes, such as CAOMT and/or CCoAOMT. An example of a genetic technique that can be used to carry out this inhibition is antisense technology, as illustrated hereinbelow. As another example, reduction in lignin content and/or alteration in lignin composition of a plant material is achieved using the technique of co-suppression, also illustrated herein. Other techniques involve genetically or biochemically manipulating the bioactivity of regulatory elements, control sequences, factors, cofactors and the like to inhibit the activity of lignin biosynthetic genes.

Genetically Engineered Plants

As used herein, the term "genetically engineered plant" refers to a plant that has been genetically manipulated. Genetic manipulation includes recombinant DNA engineering as well as other forms of altering the amount, nature, or activity of nucleic acids in a plant, such as mutagenizing plant by exposing it to a mutagen such as UV light. The term "transgenic" is used in its broadest sense and refers to an organism wherein at least one exogenous nucleotide sequence has been introduced into the cell. An "exogenous" nucleotide sequence means a nucleotide sequence that has been introduced into a cell (or an ancestor of a cell) using genetic engineering techniques. An exogenous nucleotide sequence is typically introduced into a plant cell using a vector, as described below. An exogenous nucleic acid can include a nucleic acid that is foreign, i.e., heterologous with respect to the host cell's genome; but it should nonetheless be understood that an exogenous nucleotide sequence can encode an enzyme that is endogenous to the cell into which it is introduced. For example, exogenous nucleic acids include those nucleic acids designed to overproduce endogenous enzymes, as, for example, in the technique of co-suppression as discussed below. The exogenous nucleic acid(s) in the genetically engineered plant of the invention are preferably stable and inheritable. The exogenous nucleic acids may or may not be integrated into the plant genome.

Genetically engineered plants of the invention are characterized by reduced and/or altered lignin content. Reduced and/or altered lignin composition in the genetically engineered plant is preferably attained by reducing expression of an endogenous gene involved in the lignin biosynthesis pathway, preferably the genes encoding CCoAOMT or CAOMT or both. It is known that a cell manufactures proteins by first transcribing the DNA of a gene for that protein to produce RNA (transcription). In eukaryotes, this transcript is an unprocessed RNA called precursor RNA that is subsequently processed (e.g. by the removal of introns, splicing, and the like) into messenger RNA (mRNA) and finally translated by ribosomes into the desired protein. This process may be interfered with or inhibited at any point, for example, during transcription, during RNA processing or during translation, by the presence in the cell of at least one exogenous nucleic acid. Reduced expression of the gene(s) leads to a decrease or reduction in the activity of at least one enzyme involved in the lignin biosynthesis pathway.

In a preferred embodiment, genetically engineered plants of the invention contain at least one exogenous nucleic acid associated with reduced activity in the plant of at least one biosynthetic enzyme involved in lignin biosynthesis. An exogenous nucleic acid is "associated with reduced activity" if a plant exhibits reduced activity of the biosynthetic enzyme when the exogenous nucleic acid is present, compared to the activity of the enzyme in a comparable wild-type plant, where the exogenous nucleic acid is absent. This association is not limited by or confined to any particular mechanism of action. For example, the exogenous nucleic acid could be associated with reduced activity of the enzyme by directly binding to a portion of the gene encoding the enzyme (for example, at the coding region, at a regulatory element, or the like) or an RNA transcript of the gene (for example, a precursor RNA or mRNA, at the coding region or at 5' or 3' untranslated regions); by encoding a transcript that binds to an endogenous RNA or DNA; by encoding a protein inhibitor of the enzyme; and the like. It is sufficient that the introduction of the exogenous nucleic acid into the plant cell is or can be accompanied by a reduction in the activity of the biosynthetic enzyme.

A preferred genetically engineered plant of the invention contains at least one nucleotide sequence that is "antisense" or "sense" to at least a portion of an endogenous gene involved in the lignin biosynthesis pathway. A nucleotide sequence that is "antisense to a gene" includes a nucleotide sequence that is complementary to at least a portion of the coding strand of the gene, or is complementary to at least a portion of a processed or unprocessed RNA transcript of that gene. In the case of an antisense nucleotide sequence that is complementary to at least a portion of the coding strand of the gene, the antisense nucleotide sequence is preferably operably linked to control sequences necessary to facilitate transcription of the sequence to yield an RNA transcript. It will be observed that an antisense nucleic acid that is complementary to a portion of the coding strand of a gene will typically also be complementary to a portion of the unprocessed RNA transcript of the gene. An unprocessed RNA transcript is often referred to as precursor RNA or "pre-RNA." Processed RNA transcripts include, for example, mRNA. To illustrate, antisense DNA in the form of at least a portion of the noncoding strand of the gene (or, alternatively, at least a portion of the cDNA derived from an mRNA of the gene) can be supplied as a coding strand in a construct engineered to allow transcription of the antisense DNA, and the resulting RNA transcript has the potential to interfere with the bioactivity of endogenous RNAs or DNAs, presumably via base-pairing interactions. The resulting RNA transcripts are sometimes termed "antisense RNA." An antisense RNA that is complementary to a precursor RNA can have the same nucleotide sequence as the coding DNA strand (except, of course, the U is substituted for T). An antisense RNA that is complementary to an mRNA is sometimes referred to as a messenger-RNA-interfering complementary RNA (micRNA). It should be understood that an antisense nucleotide sequence useful in the invention can be either a DNA sequence or an RNA sequence, and that transcription of an antisense DNA to yield an antisense RNA may, but need not, occur in order to affect bioactivity of a selected enzyme. Antisense nucleic acids can include naturally occurring bases or chemically or enzymatically modified bases.

Similarly, a nucleotide sequence that is in a "sense" orientation with respect to a gene includes a nucleotide sequence that is complementary to at least a portion of the noncoding or "template" strand of the gene, or is complementary to at least a portion of a cDNA derived from a mRNA transcript of the gene. A transcription product of a "sense" nucleotide sequence supplied as a coding strand is essentially identical to all or a portion of a transcription product (either processed or unprocessed, depending on the selected nucleotide sequence) of an endogenous gene.

A nucleotide sequence that is "complementary" to a nucleotide sequence (herein, the "reference" nucleotide sequence) is one that is capable of base pairing with the reference nucleotide sequence. Preferably, a complementary nucleotide sequence contains at least about 20 sequential bases that base pair with a similar number of sequential bases on the reference nucleotide sequence; more preferably, at least about 50 sequential bases on the complementary nucleotide sequence base pair with a similar number of sequential bases on the reference nucleotide sequence. For purposes of the present invention, a complementary nucleotide sequence is one that can hybridize with (i.e., form a duplex with) the reference nucleotide sequence under physiological conditions present in the host plant. It will be understood that a complementary nucleotide sequence includes, in addition to a fully complementary nucleotide sequence, a substantially complementary nucleotide sequence that contains deletions or additions of one or more bases relative to the reference sequence, provided the complementary nucleotide sequence still retains the ability to hybridize with the reference nucleotide sequence within a plant cell and affect expression of a biosynthetic enzyme.

Without intending to be bound by any theory of mechanism or mode of action, it is believed that an antisense nucleic acid, by reason of its ability to hybridize with an endogenous nucleic acid or to produce a transcript that hybridizes with an endogenous nucleic acid, inhibits or prevents further processing of the endogenous nucleic acid. Accordingly, a region of sequential bases in an antisense RNA is preferably capable of RNA base pairing with all or most of the corresponding bases in the analogous endogenous RNA sequence. It is believed that this inhibition takes place by formation of a complex between the two complementary strands of RNA, thereby interfering with production of encoded protein. How this works is somewhat uncertain; however, the formed complex potentially interferes with one or more intracellular event involving initial transcription, processing, transport or translation, or degradation of the mRNA.

RNA-RNA duplex formation and other binding interactions can be evaluated by methods well-known in the art. Inhibition or prevention of further processing of an endogenous nucleic acid is directly reflected in and evidenced by a reduction in the activity level of the encoded enzyme, which can also be measured by methods well-known in the art and also described herein. In that regard, the portion of the gene's coding strand or endogenous RNA transcript with respect to which an antisense nucleic acid is complementary includes a sufficient number of bases such that the presence of the antisense nucleic acid results in a measurable reduction in the activity level of the enzyme encoded by the gene. Typically, only a small portion of an endogenous RNA transcript needs to be recognized by a complementary antisense nucleic acid (such as an antisense RNA) in order to effect enzyme inhibition, and antisense nucleic acids comprising less than 100 nucleotides derived from the 5'-region of an endogenous mRNA are known to reduce or completely inhibit expression of the corresponding endogenous gene. On the other hand, it is preferred that a majority of the bases in the antisense nucleic acid base pair with the endogenous RNA transcript (or with a sequence in the coding strand of the gene). More preferably, all or substantially all of the bases in the antisense nucleic acid base pair with the endogenous RNA transcript or coding strand. The region of the antisense nucleic acid that is complementary to a nucleotide sequence of an endogenous or coding strand typically includes about 20 to about 1500 contiguous nucleotides, more typically at least about 100 to about 1000 contiguous nucleotides.

The exogenous nucleic acid present in the genetically engineered plant of the invention is preferably one that, when introduced into a cell, is effective to increase or decrease expression of a gene involved in lignin biosynthesis. Preferably, a exogenous nucleic acid useful in the invention contains at least one nucleotide sequence that is antisense to at least a portion of a CCoAOMT gene. In one embodiment, a portion of the RNA transcript of the exogenous nucleic acid is complementary to at least a portion of the unprocessed RNA transcript of an endogenous CCoAOMT gene (i.e., CCoAOMT precursor RNA) and/or the CCoAOMT mRNA that results from processing the CCoAOMT precursor RNA, such that CCoAOMT activity in the plant is reduced. For example, an antisense RNA transcript that is complementary to a CCoAOMT mRNA can be generated using CCoAOMT cDNA as the antisense DNA. Preferably, the CCoAOMT cDNA used as antisense DNA comprises at least a portion of a nucleotide sequence that is complementary to "sense" cDNA nucleotide sequences SEQ ID NO:2, SEQ ID NO:3, SEQ ID NO:4 or SEQ ID NO:5 (FIGS. 9–12). The portion is preferably at least about 20 nucleotides in length, more preferably at least about 50 nucleotides in length, and is most preferably the entire complementary nucleotide sequence. Preferred CCoAOMT cDNAs for use as antisense DNA also include nucleotide sequences that are complementary to at least a portion of nucleotide sequences that are substantially identical to "sense" cDNA sequences SEQ ID NOs:2–5. "Substantially identical," as that term is used herein in connection with nucleotide sequences, means at least about 80% nucleotide identity; more preferably at least about 90% identity, most preferably at least 95% identity. Nucleotide identity is defined in the context of a homology comparison between a test nucleotide sequence and a selected nucleotide sequence, such as "sense" cDNA sequences SEQ ID NOs:2–5. The two nucleotide sequences are aligned in a way that maximizes the number of nucleotides that they have in common along the lengths of their sequences; gaps in either or both sequences are permitted in making the alignment in order to maximize the number of shared nucleotides, although the nucleotides in each sequence must nonetheless remain in their proper order. The percentage nucleotide identity is the higher of the following two numbers: (a) the number of nucleotides that the two sequences have in common within the alignment, divided by the number of nucleotides in the test nucleotide sequence, multiplied by 100; or (b) the number of nucleotides that the two sequences have in common within the alignment, divided by the number of nucleotides in the selected nucleotide sequence, multiplied by 100. Nucleotide sequences that are complementary to truncated forms of "sense" cDNAs SEQ ID NOs:2–5 are also preferred for use as antisense DNA provided they are effective to cause a reduction in CCoAOMT activity in the plant.

Alternatively or additionally, a portion of the RNA transcript of the exogenous nucleic acid can be complementary to at least a portion of the unprocessed RNA transcript of an endogenous CAOMT gene (i.e., CAOMT precursor RNA) and/or the CAOMT mRNA that results from processing the CAOMT precursor RNA, such that CAOMT activity in the plant is reduced. For example, an antisense RNA transcript that is complementary to a CAOMT mRNA can be generated using CAOMT cDNA as the antisense DNA. Preferably, the CAOMT cDNA used as antisense DNA comprises at least a portion of a nucleotide sequence that is complementary to "sense" cDNA sequence SEQ ID NO: 1 (FIG. 8). The portion is preferably at least about 20 nucleotides in length, more preferably at least about 50 nucleotides in length, and is most preferably the entire complementary sequence. Preferred CAOMT cDNAs for use as antisense DNA also include nucleotide sequences complementary to at least a portion of a nucleotide sequence that is substantially identical to "sense" cDNA sequence SEQ ID NO:1. Nucleotide sequences that are complementary to truncated forms of "sense" cDNA sequence SEQ ID NO:1 are also preferred for use as antisense DNA provided they are effective to cause a reduction in CAOMT activity in the plant.

It should be noted that the various antisense sequences described herein can also be employed in a "sense" orientation, to achieve a reduction of CCoAOMT activity and/or CAOMT activity via cosuppression, as described below.

Simultaneous reduction of CCoAOMT and CAOMT enzyme activity can accomplished using a first exogenous nucleic acid having a nucleotide sequence that is "antisense" to at least a portion of an endogenous CCoAOMT gene, and a second exogenous nucleic acid having a nucleotide sequence that is "antisense" to at least a portion of an endogenous CAOMT gene sequence or CCoAOMT cDNA sequence. Alternatively, the two antisense sequences can be present within the same exogenous nucleic acid.

The RNA transcript generated by the antisense nucleotide sequence can be complementary to at least a portion of an endogenous CCoAOMT or CAOMT RNA at either a protein coding region and/or a non-coding region, such as an untranslated region on an mRNA or an intron on a precursor RNA, or it can be complementary to at least a portion of chromosomal DNA containing the CCoAOMT or CAOMT gene, so as to inhibit CCoAOMT and/or CAOMT gene expression as reflected in reduced CCoAOMT and/or CAOMT activity levels in the cells.

Preferred Methods for Preparing Genetically Engineered Plants

Genetic manipulation of CCoAOMT and/or CAOMT enzyme activity can be accomplished in accordance with the invention using a variety of methods that include, but are not limited to, "antisense" techniques as described briefly above and in more detail below, "sense" or "co-suppression" techniques, or direct manipulation of an endogenous plant gene, for example by mutating at least one control sequence that is operably linked to an endogenous coding sequence. Antisense regulation is described, for example, in Crowley et al. *Cell,* 43:633–641 (1985), which relate to the use of an antisense construct of the discoidin gene transfected into Dictyostelium to repress expression of endogenous discoidin genes. Antisense regulation has also been described by Rosenberg et al., *Nature,* 313:703–706 (1985); Preiss et al., *Nature,* 313:27–32 (1985); Melton, *Proc. Natl. Acad. Sci.,* (U.S.A.) 82:144–148 (1985); Izant and Weintraub, *Science,* 229:345–352 (1985); and Kim and Wold, *Cell,* 42:129–138 (1985). Additional methods for ulitlzing antisense nucleic acids are known in the art.

The use of antisense technology to reduce or inhibit the expression of specific plant genes has been described, for example in European Patent Publication No. 271988. Reduction of gene expression led to a change in the phenotype of the plant, either at the level of gross visible phenotypic difference, for example a lack of lycopene synthesis in the fruit of tomato leading to the production of yellow rather than red fruit, or at a more subtle biochemical level, for example, a change in the amount of polygalacturonase and reduction in depolymerisation of pectins during tomato fruit ripening (Smith et. al., *Nature,* 334:724–726 (1988); Smith et. al., *Plant Mol. Biol.,* 14:369–379 (1990)). Thus, antisense RNA has been demonstrated to be useful in achieving reduction of gene expression in plants.

In one embodiment of the method of making a plant of the invention, an exogenous DNA capable of being transcribed inside a plant to yield an antisense RNA transcript is introduced into the plant, e.g., into a plant cell. The exogenous DNA can be prepared, for example, by reversing the orientation of a gene sequence with respect to its promoter. Transcription of the exogenous DNA in the plant cell generates an intracellular RNA transcript that is "antisense" with respect to that gene.

The exogenous nucleic acid of the invention preferably comprises a promoter sequence, a coding sequence, and a terminator sequence. The term "coding sequence" is used broadly herein to mean a nucleotide sequence capable of being transcribed to form an RNA within a host cell; it is not limited to a sequence that encodes a protein. In effect, any nucleotide sequence that is operably linked to control sequences that allow it to be transcribed into an RNA transcript constitutes a "coding sequence" for purposes of this invention. The RNA transcript "encoded" by the coding sequence can, but is typically not, further processed to yield an mRNA, and typically does not encode a protein, although it can, as in the case of co-suppression as discussed in more detail below. The coding sequence of the exogenous nucleic acid preferably contains an antisense nucleotide sequence, that is, a nucleotide sequence encoding an antisense RNA transcript at least a portion of which is substantially complementary to at least a portion of an endogenous RNA transcript present in the plant. More preferably, the antisense RNA transcript is complementary to an endogenous RNA transcript of a gene that encodes an enzyme involved in lignin biosynthesis, e.g., CCoAOMT and/or CAOMT, so that, when the exogenous nucleic acid is incorporated into a plant, production of the enzyme from the endogenous gene is inhibited. Preferably, the coding sequence encodes an RNA transcript complementary to the mRNA encoded by the endogenous gene.

In another embodiment of the method of making a plant of the invention, the coding sequence of the exogenous nucleic acid is in the same orientation as the coding sequence of the endogenous gene of interest, i.e., the "sense" orientation. Providing a nucleic acid having a coding sequence in the same orientation as that of the endogenous gene in some cases leads to overproduction of the product of the endogenous gene, however in other cases is known to inhibit production of the endogenous gene (see Montgomery et al., *Trends in Genetics* 14:7, 255–258 (1998)). The latter effect is known as "co-suppression" of the endogenous gene. The biological mechanisms of co-suppression are not well understood but are thought to involve direct DNA-DNA interactions or employ an RNA effector molecule. Whether or not a gene encoding an enzyme is co-suppressed by the introduction of an exogenous nucleic acid having a sequence encoding the endogenous enzyme in a "sense" orientation is readily determinable by measuring the enzyme activity in the engineered cell and comparing it to the enzyme activity in a comparable wild-type cell.

Standard plant expression vectors and cassettes are employed to transform selected plant cells with the exogenous nucleic acid of the invention, as described in more detail below. After the cells have been transformed, the cells can be grown into plants. The invention therefore provides plant cells, and plants derived therefrom having stably incorporated in their genomes at least one exogenous nucleic acid in an antisense or sense orientation, including the fruit, seeds, and progeny of such plants that contain the exogenous nucleic acid.

Other methods for preparing the plants of the invention include, but are not limited to, mutation of a CCoAOMT and/or CAOMT gene sequence, e.g., by point mutation, or the use of an insertion transposon. For example, in vitro manipulation of an endogenous CCoAOMT gene sequence can provide a genetically engineered plant of the invention. When the altered nucleotide sequence is subsequently transformed into a plant cell or tissue, the mutated sequence can replaces an endogenous homologous sequences by homologous recombination. A resulting plant is characterized by a reduction in endogenous enzyme activities, leading to a reduced amount of lignin and/or altered lignin composition when compared to a wild-type plant.

Techniques to create a mutated nucleotide sequence include, but are not limited to, modification, e.g., chemical modification, of the DNA or RNA nucleotide sequence which results in one base in the sequence being converted to another base. For example, a "transition" point mutation would involve the substitution of one pyrimidine by the other or one purine by the other, thus a G/C pair in the nucleotide sequence can be exchanged with an A/T pair. Likewise, an A/T pair can be substituted for a G/C pair. A "transversion" mutation can be prepared wherein purine is replaced by a pyrimidine or where a pyrimidine is replaced by a purine. For example, an A/T pair can be converted to a T/A pair or a C/G pair. Additionally, endogenous gene sequences can also be directly mutated by treatment of seeds with chemical mutagens (e.g., ethyl methanesulfonate) or physical means (e.g., fast neutron or gamma ray irradiation). Alternatively, an endogenous DNA sequence can be mutated by insertion of a nucleotide sequence for a transposable element, (e.g., a maize transposon) and T-DNA (transfer DNA from Agrobacterium Ti plasmid). Insertion of such sequences or elements into an endogenous CCoAOMT nucleotide sequences yields a genetically engineered plant characterized by a reduction in CCoAOMT activity, and further characterized by a reduced amount of lignin compared to a wild-type plant.

Expression Vectors and Cassettes

Expression vectors and/or expression cassettes are useful to introduce an exogenous nucleic acid of the invention into a host plant cell or tissue. Other options include the use of "naked DNA" (or naked RNA) or constructs containing transposable elements.

Suitable vectors can be integrating or nonintegrating and include, but are not limited to, plasmids, viral vectors and cosmids. Selection of a suitable vector backbone for the invention depends upon the characteristics desired in the resulting construct, such as a selection marker, plasmid reproduction rate, and the like. When antisense technology is used, a coding sequence is inserted into an expression vector in an "antisense" orientation (see, e.g., FIG. 2) to allow for the production of an antisense transcript as described in detail above. If more than one exogenous nucleic acid is to be delivered to the cell, the exogenous nucleic acid sequences can be present on the same vector or, alternatively, on different expression vectors. Nucleotide sequences for construction of expression vectors, as well as other suitable gene sequences, are readily available to one of skill in the art from databases such as GENBANK.

A coding sequence, such as an antisense nucleotide sequence, is preferably flanked by control sequences that regulate expression of the selected nucleotide sequence(s) in a transformed plant cell. As used herein, the term "control sequence" refers to a nucleotide sequence or region that is capable of regulating transcription and/or translation of the selected coding sequence(s). Control sequences include, but are not limited to, regulatory sequences such as promoters, terminators, such as, for example, a nopaline synthase terminator derived from the *Agrobacterium tumefaciens* Ti plasmid (nos ter), polyadenylation signals and other enhancing elements known in the art. A control sequence, such as a promoter or a terminator, is "operably linked" to a nucleotide sequence if it is/does, or can be used to, control or regulate transcription and/or translation of that nucleotide sequence.

A "promoter," as used herein, is a nucleotide sequence that can initiate transcription of genetic material. Promoters act as regulatory elements to which RNA polymerase binds, and therefore initiates transcription of a downstream coding sequence. The invention is not limited by the use of any particular promoter, other than the promoter must be effective to initiate transcription of genetic material in a plant cell. Plant-specific promoters are preferred. These include, but are not limited to, tissue-specific promoters and promoters that are specific for one or more developmental phase, such as promoters that direct expression of the transgene to the developing seed.

The promoter used in the invention can be a constitutive or an inducible promoter. It can be, but need not be, heterologous with respect to the host. Promoters may be obtained from Ti- or Ri-plasmids, from plant cells, plant viruses or other hosts where the promoters are found to be functional in plants. Illustrative promoters include the octopine synthetase promoter, the nopaline synthase promoter, the manopine synthetase promoter, etc., as illustrative of promoters of bacterial origin functional in plants. Viral promoters include the cauliflower mosaic virus full length (35S) and region VI promoters, etc. Endogenous plant promoters include the ribulose-1,6-biophosphate (RUBP) carboxylase small subunit (ssu), the b-conglycinin promoter, the phaseolin promoter, the ADH promoter, heat-shock promoters, tissue specific promoters, e.g., promoters associated with fruit ripening, etc. Preferably, the promoter is selected from promoters known to operate in plants and is selected from the group consisting of CaMV35S, GPAL2, GPAL3 and endogenous plant promoter controlling expression of the gene encoding the endogenous target enzyme.

An expression vector to be introduced into the cell(s) of the invention typically contains either a selectable marker gene or a reporter gene or both, to facilitate identification and selection of transformed cells from the population of cells sought to be transformed. Alternatively, the selectable marker can be carried on a separate piece of DNA and used in a co-transformation procedure. Both selectable markers and reporter genes may be flanked with appropriate regulatory sequences to enable expression in the host cells. Useful selectable markers are well known in the art and typically include, but are not limited to, for example, antibiotic and herbicide-resistance genes, such as neo, hpt, dhfr, bar, aroA, dapA, and the like.

Transfection and Transformation

Host plant cells are transfected, and preferably transformed, with the above-described constructs or expression vectors, then cultured in conventional nutrient media modified as appropriate for inducing promoters, selecting transformants, or amplifying the genes encoding the desired sequences.

"Transfection," as used herein, refers to the introduction of an exogenous nucleic acid, typically in the form of a vector, into a host plant cell. Numerous methods of transfection are known to the ordinarily skilled artisan, for example, the calcium phosphate precipitation method and electroportation are commonly used. Successful transfection is generally recognized when any indication of the operation of the vector occurs within the host plant cell. The exogenous nucleic acid may be maintained as a non-integrated vector, for example, a plasmid, or alternatively, may be integrated into the host genome.

"Transformation," as used herein, means introducing DNA into an organism so that the DNA is replicable, either as an extra-chromosomal element or by chromosomal integrant. Depending on the host plant cell used, transformation is done using standard techniques appropriate to such cells. Infection with *Agrobacterium tumefaciens,* for example, can be used for transformation of certain plant cells. However, other methods for introducing DNA into cells such as by nuclear injection, electroportation, or protoplast fusion may also be used.

To confirm the presence of at least one exogenous nucleic acid encoding a nucleotide sequence in a host cell, a variety of assays may be performed. Such assays include, for example, Southern and Northern Blotting, RT-PCR and PCR; or biochemical assays that detect the presence or absence of an expressed polypeptide, e.g., by immunological means (ELISAs and Western blots).

Figure 2:
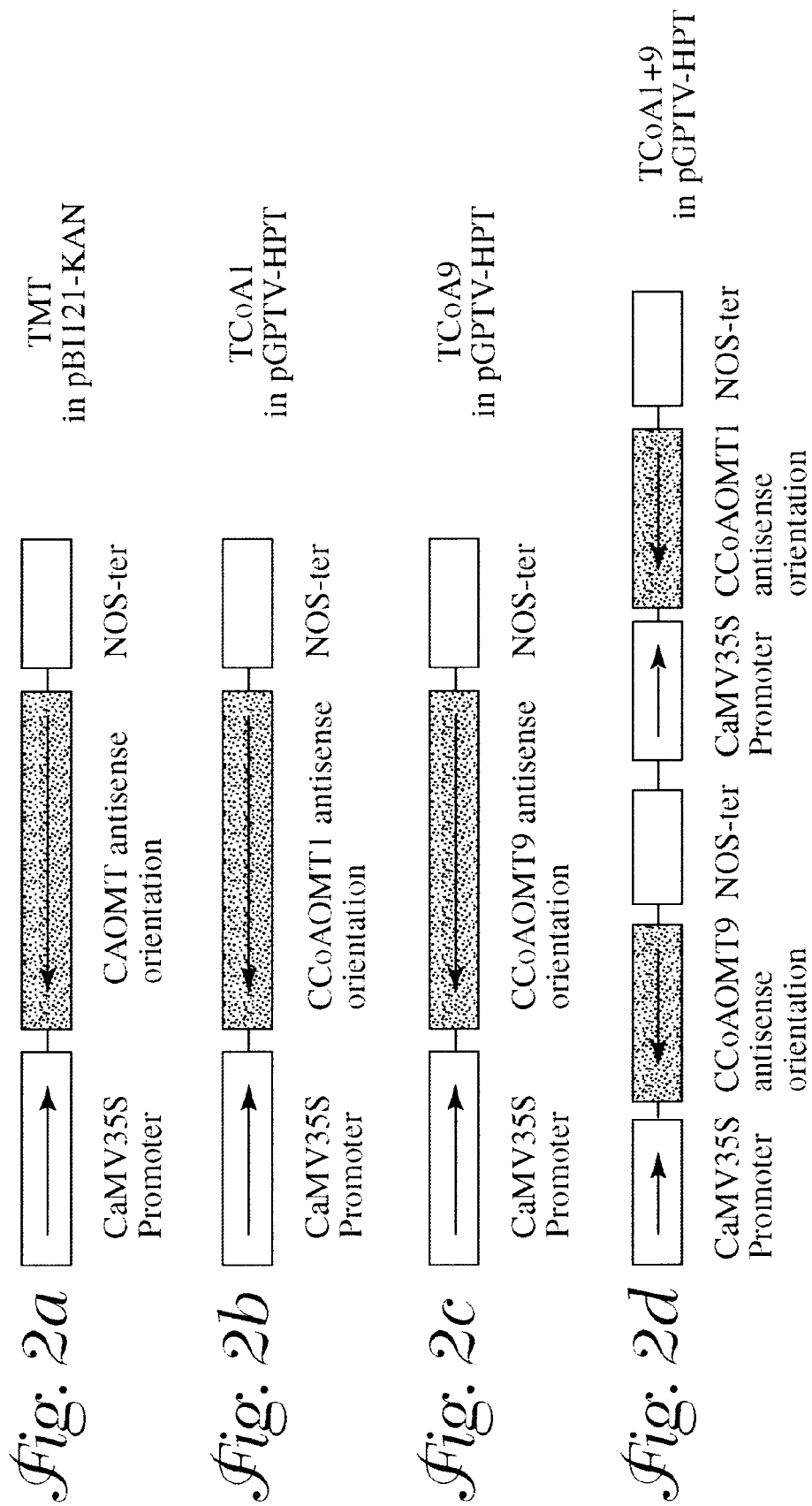
FIG. 2 shows antisense expression constructs for CCoAOMT and CAOMT.

Preferred antisense expression vectors according to the present invention are schematically illustrated in FIG. 2. Antisense constructs of the invention, include, but are not limited to, antisense constructs TCoA1, TCoA9 and TCoA1+9 prepared in binary vector pGPTV-HPT. The binary vector preferably contains a hygromycin resistance gene. The antisense construct TMT can be prepared in the binary vector pBI121-KAN, and preferably contains a kanamycin resistance gene. The antisense expression of these nucleic acids can be initiated by the cauliflower mosaic virus (CaMV) 35S promoter, and terminated by the polyadenylation signal from the nopaline synthase gene (NOS-ter) of the Agrobacterium Ti plasmid. Although there is no theoretical upper limit, it is generally convenient to use nucleotide sequences between about 20 nucleotides and about 1500 nucleotides in length. Preparation of such antisense constructs are further set forth in the Examples below.

Antisense expression vectors according to the present invention may be prepared as follows. Coding regions containing CCoAOMT and/or CAOMT nucleotide sequences can be excised by the selection of appropriate restriction enzymes known in the art. The obtained coding regions can subsequently be cloned, in antisense orientation, into a vector in a site between the desired promoter sequence (for example, CaMV 35S promoter or the bean PAL promoter (Bevan et al, *EMBO. J.,* 8:1899–1906 (1989))), and the desired terminator sequence (for example the terminator of the *Agrobacterium tumefaciens* nopaline synthase gene). Fragments containing the coding region flanked by the promoter and terminator sequences are typically cloned into a suitable vector, such as the binary vector pGPTV-HPT, as described above, which contains a hygromycin resistance gene. See generally Sambrook et al., *Molecular Cloning: A Laboratory Manual* (1989).

The invention will be further described by reference to the following detailed examples which are exemplary and not intended to limit the invention.

EXAMPLES

Example 1

Isolation of Tobacco CCoAOMT and CAOMT cDNAs

Tobacco plants (*Nicotiana tabacum* cv Xanthi) were grown in a greenhouse environment. Tobacco cDNAs were synthesized from mRNAs isolated from stems of the tobacco plants and were ligated into the cloning vector Lambda ZAPII (λZAPII) (Stratagene, La Jolla, Calif.) to generate a tobacco stem cDNA library. The cDNA library was used for immunoscreening of CCoAOMT and CAOMT cDNAs with antibodies against zinnia CCoAOMT and antibodies against zinnia CAOMT (polyclonal antibodies prepared by immunization of rabbits with zinnia CCoAOMT and CAOMT proteins according to the procedure described by Harlow et al., *Antibodies: A Laboratory Manual* (1988)), respectively.

Positive clones were identified and converted into phagemid. The cDNAs were sequenced in both the 5' and 3' directions. One CAOMT sequence (SEQ ID NO: 1, FIG. 8) and four different CCoAOMT sequences (SEQ ID NOs: 2–5, FIGS. 9–12) were identified. A comparison of the cDNA sequences against the data bank (GENBANK) was performed using the BLAST network service from the National Center for Biotechnology Information (Bethesda, Md.). The substrate caffeoyl CoA was synthesized as described by Negrel et al., *Phytochemistry,* 23:31–34 (1984).

Example 2

Construction of Vectors for Antisense Expression of CCoAOMT cDNA and CAOMT cDNA

Sequence analysis of the four different CCoAOMT cDNAs identified in Example 1 demonstrated that the four CDNA sequences could be divided into two groups according to the degree of nucleotide sequence identity. The cDNAs CCoAOMT1 and CCoAOMT2 were designated as group-I, and the cDNAs CCoAOMT3, and CCoAOMT9 were designated as group-II. Within the same group, the CCoAOMT cDNAs shared more than 94% sequence identity. An 87% sequence identity existed between the two groups. To ensure a high efficiency of antisense inhibition, one CCoAOMT cDNA was selected from each group, i.e., CCoAOMT1 from group-I (SEQ ID NO: 2) and CCoAOMT9 from group-II (SEQ ID NO: 5) to prepare expression vectors for antisense expression. FIG. 13 shows an alignment of the coding regions of CCoAOMT1 and CCoAOMT9 cDNAs.

The antisense expression construct TMT (FIG. 2(a)), designed to inhibit the expression of CAOMT, was constructed in the binary vector pBI121-KAN, which contains the kanamycin resistance gene. Specifically, a CAOMT CDNA fragment (SEQ ID NO: 1) was inserted in the EcoRI site of pBluescript plasmid using EcoRV and SacI. The excised fragment was then ligated into the SmaI and SacI sites of the binary vector pBI121 (Clontech, Palo Alto, Calif.) to create the antisense expression construct TMT.

Three antisense expression vectors designed to inhibit expression of CCoAOMT were constructed in the binary vector of pGPTV-HPT which contains a hygromycin resistance gene. A first construct TcoA1 (FIG. 2(b)), designed for antisense expression of CCoAOMT-1 cDNA (SEQ ID NO: 2), was created by amplifying a CCoAOMT-1 cDNA fragment using polymerase chain reaction (PCR) with two primers:
5'-TTGCTTGATATCATGGCTGAGAACGGTGCAGCAC-3' (SEQ ID NO: 8) and 5'-TTGCTTACTAGTCAGTGCTGATGCGGCGGCACA-3' (SEQ ID NO: 9). The following parameters were used for PCR amplification of specific DNA: 30-seconds denaturation at 94° C., 30-seconds annealing at 55° C., and 2-minutes elongation at 72° C.; for 30 cycles. The amplified fragment was cut with SpeI and EcoRV restriction enzymes, and ligated into the SpeI and EcoRV sites of pBI221 vector (Clontech, Palo Alto, Calif.) to make a first shuttle construct pBI221-TCoA1AS.

The CCoAOMT-1 cDNA in combination with the CaMV35S promoter (present in pBI221 vector) and the nopaline synthase (NOS) terminator (present in pBI221 vector) was then isolated from pBI221-TCoA1AS by digestion with EcoRI, filling in with the Klenow fragment of DNA polymerase I (Promega, Madison, Wis.), and then digested with PstI. The fragment was isolated and ligated into the PstI and EcoRV sites of pBluescript plasmid vector to create a second shuttle construct pBS-35STCoA1AS.

The final TCoA1 antisense expression construct was prepared utilizing the CCoAOMT-1 CDNA in combination with the CaMV35S promoter and NOS terminator in the second shuttle construct pBS-35STCoA1AS. The fragment was excised from the pBS-35STCoA1AS construct by XhoI and SmaI restriction enzymes, and ligated into the SalI and end-filled EcoRI sites of the binary vector pGPTV-HPT (Becker et al., Plant Mol. Biol., 20:1195–1197 (1992)) to create the antisense expression construct TCoA1 (FIG. 2(b)).

A second construct, TCoA9 (FIG. 2(c)), designed for antisense expression of CCoAOMT-9 CDNA (SEQ ID NO: 5), was created by amplifying a CCoAOMT-9 cDNA fragment using PCR with two primers: 5'-TTGCTTGATATCATGGCAGAGAACGGAATTAAAC-3' (SEQ ID NO: 10) and 5'-TTGCTTACTAGTCAGTGCTGATGCGGCGGCACA-3' (SEQ ID NO: 11). The same strategy utilized for construction of the TCoA1 expression cassette was employed to ligate the amplified CCoAOMT-9 cDNA fragment into the binary vector pGPTV-HPT to prepare the antisense expression construct TCoA9.

A third construct, TCoA1+9 (FIG. 2(d)), designed for antisense expression of both CCoAOMT-1 (SEQ ID NO: 2) and CCoAOMT-9 (SEQ ID NO: 5) cDNAs was prepared as follows. The CCoAOMT-9 cDNA fragment combined with the CaMV35S promoter and the NOS terminator, was excised from the pBS-35STCoA9AS construct by initial digestion with SalI, filling in with the Klenow fragment of DNA polymerase I, and then digestion with XbaI. This fragment was then ligated into the SmaI and XbaI sites of the plasmid pBS-35STCoA1AS. The DNA fragment containing both the CCoAOMT-1 and CCoAOMT-9 antisense cassettes was excised by XhoI and SmaI, and then ligated into the SalI and end-filled EcoRI sites of the binary vector pGPTV-HPT to make the antisense expression construct TcoA1+9.

Antisense expression of the cDNAs in these constructs is driven by the cauliflower mosaic virus (CaMV) 35S promoter and terminated by the polyadenylation signals from the no paline synthase gene (NOS-ter) of the Agrobacterium Ti plasmid (FIG. 2).

Example 3

Tobacco Transformation and Regeneration

Constructs TMT, TCoA1, TCoA9 and TCoA1+9 were transformed into Agrobacterium tumefaciens LBA4404 (Clontech, Palo Alto, Calif.) by electroportation. Tobacco (Nicotiana tabacum cv Xanthi) leaf discs were transformed with Agrobacterium as described by Horsch et al., Science, 227:1229–1231(1985). The TMT transformants were selected by growing on the Murashige and Skoog medium (Sigma, St. Louis, Mo.) containing 300 milligrams/liter (mg/L) kanamycin (Sigma) and 500 mg/L carbenicillin (Sigma). The TCoA transformants were selected by growing on the Murashige and Skoog medium containing 50 mg/L hygromycin (Sigma) and 500 mg/L carbenicillin. The transformed tobacco shoots were allowed to root on the Murashige and Skoog medium, and were subsequently transferred to soil and grown in the greenhouse. Transformed plants were screened for a reduction in O-methyltransferase (OMT) activities.

Example 4

Preparation of Crude Extracts and Assay of Enzyme Activity

Tobacco stems from the transformed plants above in example 3 were homogenized in an extraction buffer (50 millimolar (mM) Tris-HCl (Sigma), pH 7.5, 0.2 mM magnesium chloride ($MgCl_2$) (Sigma), 2 mM dithiotreitol DTT (Sigma), 10% glycerol (Sigma), 0.2 mM phenylmethylsulfonyl fluoride (PMSF) (Sigma), 10 micrograms/milliliter ($\mu$g/mL) leupeptin (Sigma), 10 $\mu$g/mL aprotinin (Sigma)) with a mortar and pestle as described in Pakusch et al.,Arch. Biochem. Biophy., 271:488–494 (1989). After homogenization in the extraction buffer, the extracts were centrifuged at 12,000 g for 15 minutes. The resulting crude protein extracts were utilized in the assays described below.

CCoAOMT activity was determined essentially as described by Pakusch et al., Arch. Biochem. Biophy., 271:488–494 (1989). Briefly, fifty microliters ($\mu$l) of a reaction mixture containing 50 mM Tris-HCl, pH 7.5, 0.2 mM $MgCl_2$, 2 mM DTT, 10% glycerol, 0.2 mM PMSF, 10 $\mu$g/mL leupeptin, 10 $\mu$g/mL aprotinin, 2 nmol caffeoyl-CoA, 2 nanomoles (nmol) methyl-$^{14}$C—S-adenosylmethionine (SAM), and 20 $\mu$g of crude protein extract from above were incubated at 30° C. for 15 minutes. The reaction mixture omitting either caffeoyl-CoA or crude extract were used as blanks. The reaction was stopped by addition of 5.5 $\mu$L of 5 normal (N) NaOH (Sigma), and CoA ester was hydrolyzed by incubation of the reaction at 40° C. for 15 minutes. After hydrolysis, the reaction was acidified by addition of 6.2 μL of 6 N HCL (Sigma). The hydrolyzed product (ferulic acid) was separated from methyl-$^{14}$C-SAM by extraction with 200 μL of ethyl acetate (Sigma). The extracted products in ethyl acetate were taken for radioactivity counting in a Beckman liquid scintillation counter (Beckman, Palo Alto, Calif.).

CAOMT activity was assayed in 50 μL of reaction mixture (50 mM Tris-HCl, pH 7.5, 0.2 mM MgCl$_2$, 2 mM DTT, 10% glycerol, 0.2 mM PMSF, 10 μg/mL leupeptin, 10 μg/mL aprotinin, 2 nmol caffeic acid, 2 nmol methyl-$^{14}$C-SAM, 20 μg crude protein extract). The reaction mixture was incubated at 30° C. for 15 minutes, then stopped by addition of 1 μL of 6 N HCl. The acidified reaction mixture was extracted with 200 μL of ethyl acetate to separate the reaction product (ferulic acid) from methyl-$^{14}$C-SAM. The extracted ferulic acid in ethyl acetate was taken for radioactivity counting in a Beckman liquid scintillation counter. Final protein concentration was determined according to the Bradford method (Bradford, *Anal. Biochem.*, 72:248–254 (1976) with BSA (Sigma) as the standard protein.

Example 5

Analysis of Transgenic Plants

Western Blot Analysis

Proteins were separated on 4–20% gradient SDS-polyacrylamide gels and electro-transferred onto nitrocellulose membranes. The membranes were incubated in the blocking buffer (20 mM Tris-Cl, pH 7.6, 137 mM NaCl (Sigma), 5% non-fat milk) for 4 hours and then incubated with polyclonal antibodies against CCoAOMT or CAOMT fusion protein (polyclonal antibodies prepared by immunization of rabbits with zinnia CCoAOMT and CAOMT proteins according to the procedure described by Harlow and Lane, *Antibodies. A Laboratory Manual* (1988)) (1:5,000 dilution) in the blocking buffer overnight. In the control, the antibodies were replaced with preimmune serum (serum from the rabbits before immunization). After washing, the membranes were incubated with peroxidase-conjugated goat-anti-rabbit polyclonal antibodies (Sigma) (1:10,000 dilution in the blocking buffer) for 1 hour. The signals were detected with the Amersham ECL chemiluminescent reaction reagents according to the manufacturer's protocol (Amersham, Arlington Heights, Ill.).

Determination of Lignin Content and Composition

Lignin content was quantitatively measured using the Klason method (Kirk et al., *Methods in Enzymol.*, 161:87–101(1988)). Briefly, stems were ground into fine powder. After extraction four times in methanol and vacuum-dried, 200 milligrams (mg) of the sample was hydrolyzed in 4 mL of 72% H$_2$SO$_4$ (Sigma) at 30° C. for 1 hour. The hydrolysate was diluted with addition of 112 mL H$_2$O and then autoclaved for 1 hour. The sample solution was filtered through a fritted glass crucible. After washed and dried, the lignin was measured and expressed as a percentage of the original weight of cell wall residues.

Lignin composition was determined as described by Akin et al., *J. Sci. Food Agric.*, 63:339–347 (1993). The methanol-extracted stem samples were hydrolyzed in 4 N NaOH at 170° C. for 135 minutes. The hydrolysates were acidified with 2 N HCl to a pH of 2.0. The released lignin monomers were extracted into diethylether (Sigma) and vacuum-dried. The residue was dissolved in 10 μl pyridine (Sigma) and 10 μl N,O-bis(trimethylsilyl) trifluoroacetamide (Sigma) and analyzed for phenolics by gas-liquid chromatography.

In-source Pyrolysis Mass Spectrometry

In-source pyrolysis mass spectrometry was performed on a Finnigan GCQ equipped with a direct exposure probe (rhenium loop) (Thermoquest, San Jose, Calif.). Methanol-extracted stem samples were suspended in distilled water using a glass mortar and pestle. A small amount of the suspension was placed on the loop and the water was evaporated under vacuum. The following analysis conditions were utilized: ionization energy 22 eV; mass range 50–500; scan time 1 second; temperature rise about 10° C./second to 700° C.; ion source temperature 175° C.

Histological Staining of Lignin

Histological staining of lignin was performed. Briefly, tobacco stems were free-hand sectioned with a razor blade, and the resulting sections were stained for total lignin with phloroglucinol-HCl (1% phloroglucinol in 6N HCl). The histologically stained sections were observed under a dissection microscope using dark-field illumination.

Example 6

Generation of Transgenic Plants with a Reduction in CCoAOMT

Figure 3:
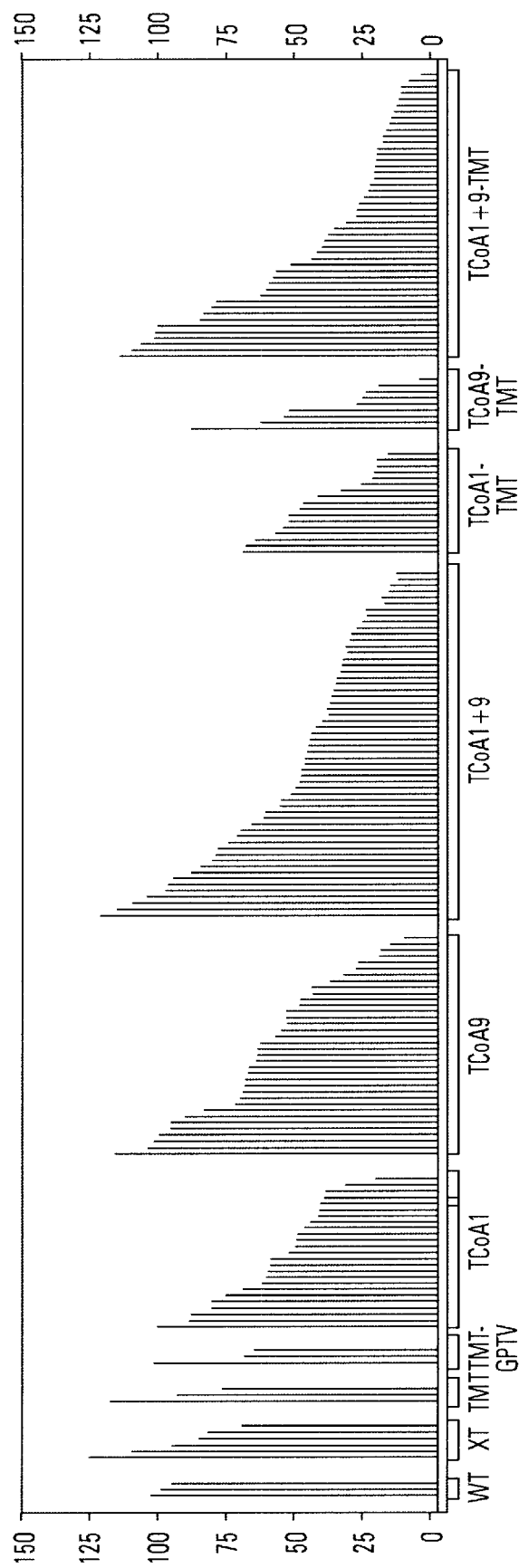
FIG. 3 shows CCoAOMT activity in transgenic tobacco plants: WT, wild type; XT-GPTV, wild type transformed with the binary vector pGPTV-HPT alone; TMT, plants with antisense expression of CAOMT; TMT-GPTV, TMT transformants re-transformed with pGPTV-HPT vector alone; TCoA1, plants with antisense expression of CCoAOMT1 alone; TCoA9, plants with antisense expression of CCoAOMT9 alone; TCoA1+9, plants with antisense expression of both CCoAOMT1 and CCoAOMT9; TCoA1-TMT, plants with antisense expression of both CCoAOMT1 and CAOMT; TCoA9-TMT, plants with antisense expression of both CCoAOMT9 and CAOMT; TCoA1+9-TMT, plants with antisense expression of CCoAOMT1, CCoAOMT9 and CAOMT.
Figure 4:
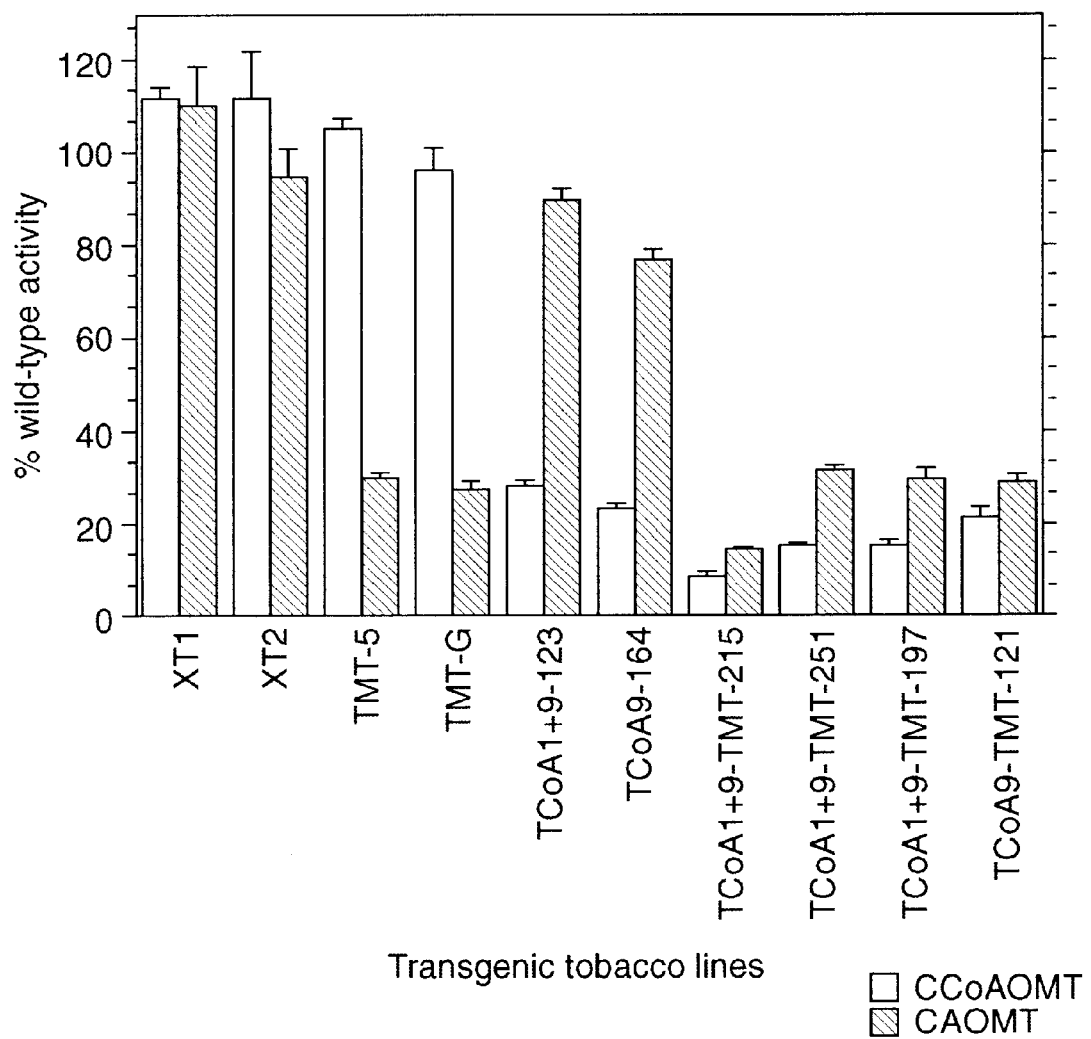
FIG. 4 shows CCoAOMT and CAOMT enzyme activities in transgenic tobacco plants; figure legend is set forth in FIG. 3.

As shown in FIG. 3, of the 120 transgenic plants analyzed, 43% of the transgenic plants showed a greater than 50% reduction of CCoAOMT enzymatic activity. Based in part on these results, two specific lines TCoA9-164 and TCoA1+9-123 (numbers 164 and 123 are transgenic line numbers) were selected for further analysis. Basal stems of mature plants were used for CCoAOMT activity assay. CCoAOMT activity in the wild-type plants was expressed as 100%. CCoAOMT activity in the transgenic plants was expressed as a percentage of wild-type activity. As shown in FIG. 4, CCoAOMT activity in TCoA9-164 and TCoA1+9-123 lines was reduced to 23% and 28% that of the wild-type, respectively. However, the CAOMT enzymatic activity was not changed in the transgenic plants (FIG. 4).

Western blot analysis was employed to confirm the activity assay results described above. The intensity of the two specific bands recognized by the antibodies against CCoAOMT was significantly reduced in the TCoA9-164 and TCoA1+9-123 lines compared to that of the wild type. Because the proteins encoded by group-I CCoAOMT genes are about 1 kD bigger than those encoded by group-II CCoAOMT genes, the upper band on the Western blot corresponded to group-I CCoAOMT, and the lower band corresponded to group-II CCoAOMT.

A simultaneous reduction in both bands in the TCoA9-164 line demonstrated that antisense expression of the CCoAOMT9 construct was sufficient for suppression of all CCoAOMT activity, although the two groups of CCoAOMTs share about 87% of DNA sequence identity. However, the upper band was preferentially suppressed in the examined transgenic plants. Consistent with the CAOMT activity assay, the intensity of the band recognized by the antibodies against CAOMT was the same as that of the wild type. These results demonstrated that expression of the CCoAOMT antisense cDNAs results in specific reduction in CCoAOMT expression.

The transgenic plants TCoA9-164 and TCoA1+9-123 were further examined for insertion of the antisense expression cassettes into the plant genome. A CCoAOMT1 specific primer
5'-TTGCTTGATATCATGGCTGAGAACGGTGCAGCAC-3' (SEQ ID NO: 8) or a CCoAOMT9 specific primer 5'-TTGCTTGATATCATGGCAGAGAACGGAATTAAAC-3'

(SEQ ID NO: 10) together with a primer 5'-CCTTCGCAAGACCCTTCCTC-3' (SEQ ID NO: 12) corresponding to the CaMV35S promoter region were used to amplify respective sequences in the transgenic plants. PCR amplification parameters were as described in Example 2. The results (FIG. 6) showed that TCoA9-164 line had only CCoAOMT9 antisense cDNA, and TCoA1+9-123 had both CCoAOMT1 and CCoAOMT9 antisense cDNAs, consistent with the sequence in the vectors used for transformation. Genomic DNA isolated from the wild-type plants did not show any amplification with these primers.

Example 7

Generation of Transgenic Plants with a Reduction in Both CCoAOMT and CAOMT

To examine the effects of a reduction in both CCoAOMT and CAOMT activities on lignin biosynthesis, vectors containing CCoAOMT and CAOMT antisense cDNA cassettes were introduced into tobacco plants. This was accomplished by first introducing the TMT construct into the wild-type plants to create a TMT transgenic plant line having about 30% wild-type CAOMT activity. The TCoA1, TCoA9 or TCoA1+9 constructs were then introduced into the TMT line. As shown in FIG. 3, of the 73 transgenic plants analyzed, 59% of the transgenic plants exhibited over a 50% reduction in CCoAOMT activity.

Next, four transgenic plant lines TCoA1+9-TMT-197, TCoA1+9-TMT-215, TCoA1+9-TMT-251, and TCoA9-TMT-121) (numbers 121, 197, 215 and 251 are the transgenic line numbers) were selected for further analysis. As shown in FIG. 4, the observed CCoAOMT enzyme activity was 8–21% of the wild-type activity in these transgenic plants. The CAOMT activity was 14–31% of the wild-type activity in these transgenic plants.

Figure 5:
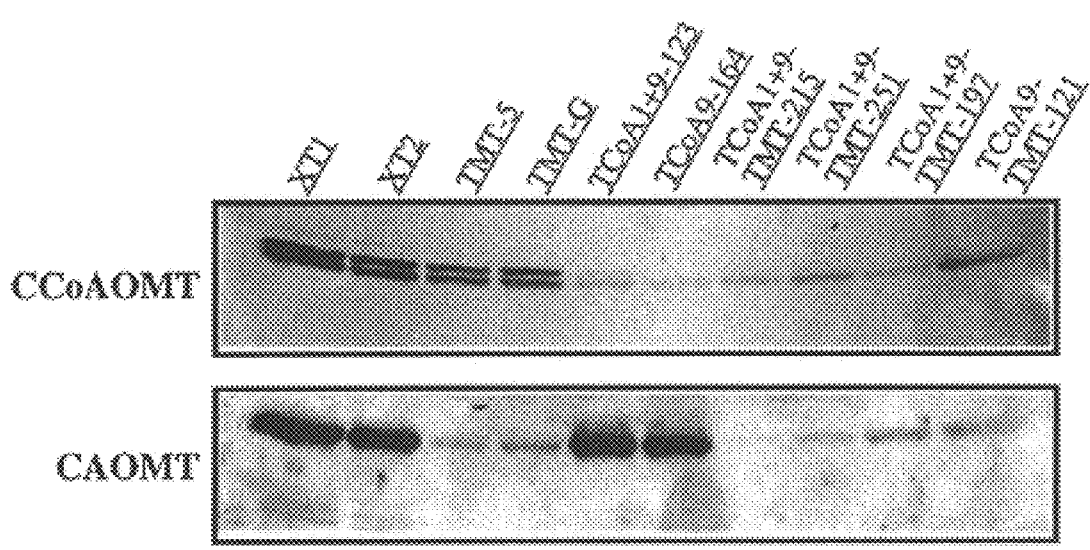
FIG. 5 shows a Western blot analysis of CCoAOMT and CAOMT proteins in transgenic tobacco plants; figure legend is set forth in FIG. 3.

Western blot analysis of CCoAOMT and CAOMT protein expression was also performed. Ten-microgram of protein extracted from old stems was loaded in each lane. The blot was probed with either antibodies against zinnia CCoAOMT or antibodies against zinnia CAOMT. Reduction of OMTs was evident in transgenic lines, consistent with the activity assay results. Two bands were seen in the CCoAOMT blot. The top band corresponded to CCoAOMT9, and the lower band corresponded to CCoAOMT1. Western blot analysis thus showed that the intensity of both the CCoAOMT and CAOMT bands was significantly reduced (FIG. 5), which was consistent with the activity assay results.

Figure 6:
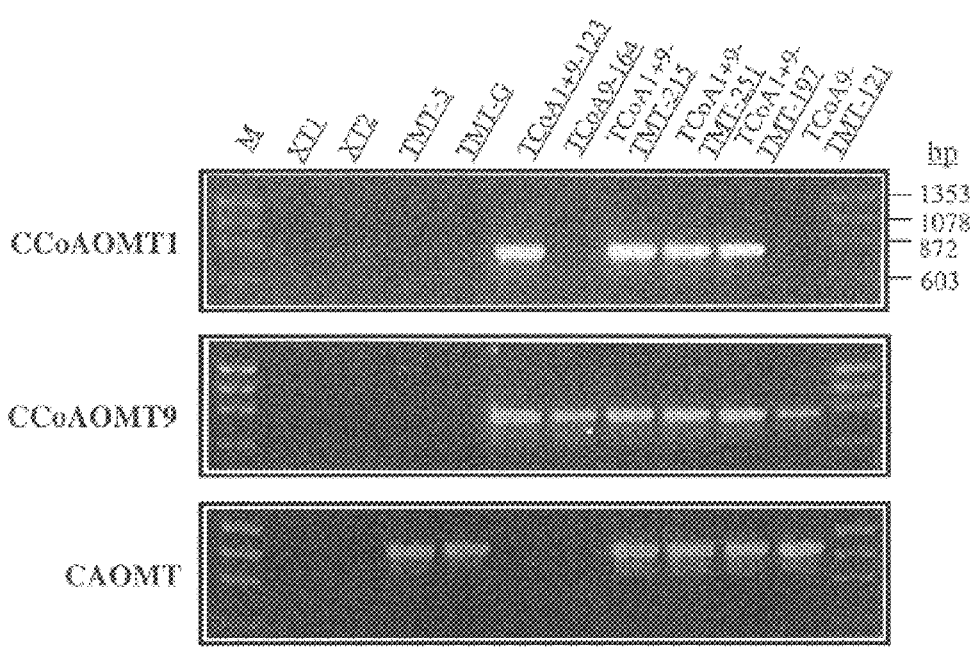
FIG. 6 illustrates the successful expression of antisense O-methyltransferase (OMT) vectors in transgenic plants; figure legend is set forth in FIG. 3.

Transgenic plants were also examined for the insertion of the antisense O-methyltransferase cassette into the genome. Genomic DNA from the transgenic plants was used in a polymerase chain reaction with a CAOMT specific primer 5'-GCCTATGGAATGACAGCATTTGAG-3' (SEQ ID NO: 13), a CCoAOMT1 specific primer 5'-TTGCTTGATATCATGGCTGAGAACGGTGCAGCAC-3' (SEQ ID NO: 8), or a CCoAOMT9 specific primer 5'-TTGCCTGATATCATGGCAGAGAACGGAATTAAAC-3' (SEQ ID NO: 10) together with a primer 5'-CCTTCGCAAGACCCTTCCTC-3' (SEQ ID NO: 12) corresponding to the CaMV35S promoter region. PCR amplification parameters were as described in Example 2. Consistent with the sequence in the vectors used for transformation, TCoA1+9-TMT-197, TCoA1+9-TMT-215 and the TCoA1+9-TMT-251 transgenic lines all had antisense sequences of CCoAOMT1, CCoAOMT9 and CAOMT. TCoA9-TMT-121 had antisense sequences of both CCoAOMT9 and CAOMT (FIG. 6). The results confirmed the insertion of antisense O-methyltransferase expression cassettes into the plant genome. The wild-type plants did not show any amplification with these primers.

Example 8

Reduction in CCoAOMT Decreases Lignin Content and Alters Lignin Composition

To examine if a reduction in CCoAOMT enzyme activity had any effect on lignification, stems of the transgenic lines TCoA9-164 and TCoA1+9-123 were collected for assay of lignin content and composition. Quantitative measurement of the Klason lignin (total lignin amount present in cell walls; Kirk et al., *Methods in Enzymol.* 161:87–101(1988)) showed that in the TCoA9-164 and TCoA1+9-123 transgenic lines, lignin content was reduced to 53% and 67% that of the wild type, respectively (Table 1).

TABLE 1

Lignin content and composition in the wild-type and transgenic tobacco plants

| | Klason lignin[a] | | Lignin composition (mg/g cell wall)[b] | | |
|---|---|---|---|---|---|
| Transgenic lines | % of cell wall[c] | % of wild-type Klason lignin | Guaiacyl lignin[c] | Syringyl lignin[c] | S/G[d] |
| XT1 | 17.3 +/− 0.9 | 94 | 17.51 +/− 2.98 | 12.26 +/− 2.03 | 0.70 |
| XT2 | 18.1 +/− 0.4 | 100 | 16.98 +/− 0.72 | 13.38 +/− 0.65 | 0.79 |
| TMT-5 | 16.3 +/− 0.6 | 89 | 15.53 +/− 1.12 | 0.89 +/− 0.34 | 0.058 |
| TMT-G | 16.3 +/− 0.6 | 89 | 16.99 +/− 1.10 | 1.99 +/− 0.11 | 0.12 |
| TCoA1 + 9 − 123 | 11.9 +/− 0.2 | 67 | 8.13 +/− 0.69 | 7.37 +/− 1.2 | 0.91 |
| TCoA9 − 164 | 9.7 +/− 0.6 | 53 | 8.21 +/− 0.52 | 8.64 +/− 0.42 | 1.05 |
| TCoA1 + 9 − TMT-215 | 6.2 +/− 0.2 | 34 | 8.54 +/− 0.53 | 2.00 +/− 0.08 | 0.23 |
| TCoA1 + 9 − TMT-251 | 7.7 +/− 0.8 | 42 | 8.46 +/− 0.02 | 1.36 +/− 0.31 | 0.16 |
| TCoA1 + 9 − TMT-197 | 7.7 +/− 0.4 | 42 | 4.06 +/− 0.83 | 2.36 +/− 0.09 | 0.58 |
| TCoA9 − TMT-121 | 10.7 +/− 0.5 | 59 | 16.18 +/− 2.14 | 2.47 +/− 0.4 | 0.15 |

[a]Klason lignin was assayed according to Kirk and Obst (1988).
[b]Lignin monolignol composition was analyzed according to Akin et al. (1993).
[c]Each data point was the mean +/− SE of two separate assays.
[d]G is the sum of vanillin, acetovanillin and vanillic acid. S is the sum of syringaldehyde, acetosyringaldehyde and syringic acid.

The results shown in Table 1 indicate that reduction of CCoAOMT enzyme activity alone is sufficient to decrease lignin content, and that the CAOMT-mediated methylation pathway does not compensate for the loss of CCoAOMT activity.

To further examine whether a decrease in lignin content was accompanied with a reduction in both guaiacyl lignin and syringyl lignin, lignin composition was analyzed in both wild-type and transgenic plants. The results depicted in Table 1 show that a reduction in CCoAOMT activity results in a decrease in both guaiacyl lignin and syringyl lignin. In the TCoA9-164 and TCoA1+9-123 transgenic lines, guaiacyl lignin was reduced to about 50% of that found in the wild-type plant, and syringyl lignin was decreased to about 60% of that found in the wild-type plant. This differential decrease of guaiacyl and syringyl lignin led to an increase in the syringyl/guaiacyl (S/G) ratio from about 0.75 found in the wild-type plant to an S/G ratio of about 0.95 in the transgenic plants.

Example 9

Effects of a Simultaneous Reduction in Both CCoAOMT and CAOMT Activity on Lignification To examine the effect of a reduction in both CCoAOMT and CAOMT on lignin content and composition, the transgenic lines TCoA1+9-TMT-197, TCoA1+9-TMT-215, TCoA1+9-TMT-251 and TCoA9-TMT-121 were used for assay of the Klason lignin and lignin composition (Table 1). The Klason lignin in these transgenic lines was reduced to amounts ranging from 34–59% that of the wild type.

Figure 7:
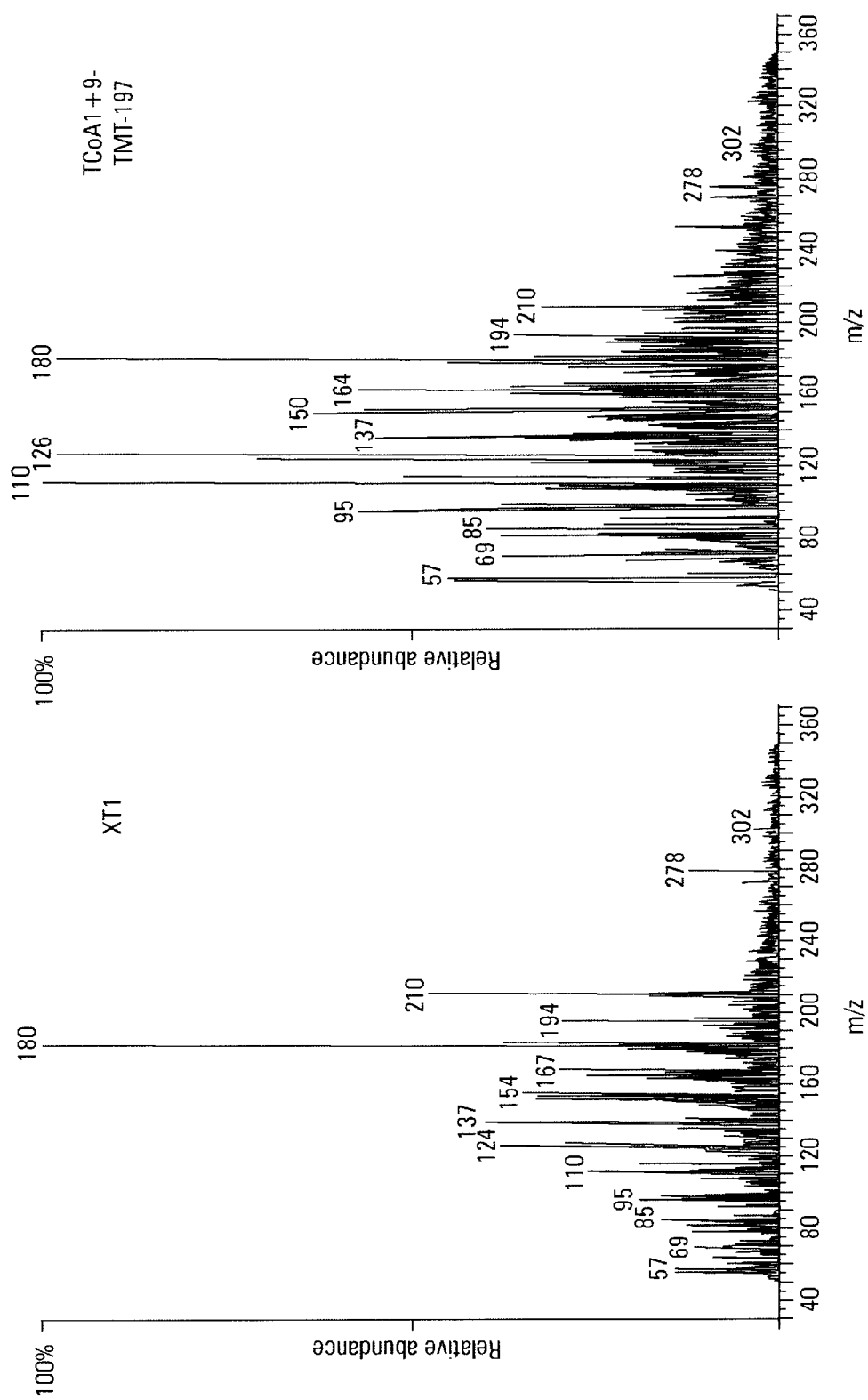
FIG. 7 shows the in-source pyrolysis mass spectrometry of cell walls of a wild-type and a transgenic plant.

The reduction in lignin in the transgenic line TCoA1+9-TMT-197 was also revealed by pyrolysis mass spectrometry (FIG. 7), a technique that has been used to evaluate a number of agricultural products. In-source pyrolysis mass spectrometry was performed using a Finnigan GCQ equipped with a direct exposure probe (rhenium loop) as described by Morrison and Archibald, J. Agri. Food Chem., 46:1870–1876 (1998). Mass peaks of guaiacyl lignin had an m/z of 124, 137, 138, 150,152, 164, 166, 178, and 180. Mass peaks of syringyl lignin had an m/z of 154, 167, 168, 180, 182, 194, 196, 208, and 210. Mass peaks of cellulose and amylose had an m/z of 57, 60, 73, 85, 86, 96, 98, 100, 102, 110, 112, 126, and 144. Mass peaks of hemicellulose had an m/z of 58, 85, 86, and 114. The relative intensity of mass peaks for lignin over mass peaks for cellulose, amylose or hemicellulose was dramatically reduced in the transgenic line TCoA1+9-TMT-197 compared to that of the wild type, indicating that the lignin content relative to the cell wall polysaccharides was much lower in TCoA1+9-TMT-197 than in the wild type.

Lignin composition analysis showed that a simultaneous reduction in both CCoAOMT and CAOMT in the lines TCoA1+9-TMT-197, TCoA1+9-TMT-215, and TCoA1+9-TMT-251 had combinational effects. In addition to the decrease in guaiacyl lignin, syringyl lignin was reduced to about 15% that of the wild type. In the line TCoA1+9-TMT-197, both guaiacyl and syringyl lignin monomers were further reduced compared to the lines with the suppression of CCoAOMT alone (TCOA9-164 and TCOA1+9-123). Guaiacyl lignin was reduced to 24% that of the wild type in TCoA1+9-TMT-197.

Example 10

Effects of Lignin Reduction on Vessel Anatomy and Plant Growth

As lignin provides mechanical strength to walls of conducting cells, the effect of lignin reduction (as described above) on vessel anatomy was examined. The stems (two stems from each transgenic line used) from both wild-type plants and transgenic plants were stained with phloroglucinol-HCl (Sigma). In the wild-type plants and transgenic plants exhibiting a reduction in CAOMT activity only (TMT lines) the vessel walls were observed to be circular or oval in shape. However, vessel walls were deformed to various degrees in the transgenic plants examined having a reduction in only CCoAOMT activity and in plants having a reduction in both CCoAOMT and CAOMT activities.

Significant deformation of the vessel walls were observed in the transgenic plant lines TCoA1+9-TMT-197, TCoA1+9-TMT-215, TCoA1+9-TMT-25 1, as the majority of vessels in the primary xylem were severely crushed and vessels in secondary xylem also frequently collapsed inward.

The wild-type plants and transgenic plants were grown to maturity in the greenhouse. All plants grew to about the same height, exhibited similar growth rates, and flowered at approximately the same time. No visible abnormal growth was observed in the transgenic plants, even in the TCoA1+9TMT-215 transgenic line that exhibited only 34% of wild-type Klason lignin content. Thus, although the resulting transgenic plants had a 40–60% lignin content reduction, they appeared to grow normally under greenhouse conditions.

Example 11

Elucidation of the CCoAOMT and CAOMT Role in Lignin Biosynthesis

The participation of CCoAOMT-mediated methylation pathway in monolignol biosynthesis has been demonstrated herein by antisense suppression of the endogenous CCoAOMT expression. For example, in a transgenic plant line with 23% of the wild-type CCoAOMT activity, the Klason lignin (Kirk et al., Methods in Enzymol., 161:87–101 (1988)), i.e., total lignin amount present in cell wall, was reduced to 53% that of the wild-type (Table 1). This indicates that a reduction in CCoAOMT alone is sufficient to decrease lignin content, and that the CAOMT-mediated methylation pathway does not compensate for the loss of CCoAOMT activity. Surprisingly, this is in sharp contrast to the effects observed from a reduction in CAOMT alone, which did not show a significant reduction in lignin content (Atanassova et al., Plant Journal, 8:465–477 (1995)). As shown herein, it appears CCoAOMT efficiently compensates for the loss of CAOMT to synthesize normal level of the Klason lignin.

As shown in Table 1 below, a reduction in lignin in the antisense CCoAOMT plant lines is accompanied with a decrease in both guaiacyl lignin and syringyl lignin. This result provides evidence that endogenous CCoAOMT is involved in the methylation of both caffeoyl-CoA and 5-hydroxyferuloyl CoA. Additionally, lignin composition analysis in transgenic plants showed that guaiacyl lignin is preferentially decreased over syringyl lignin, which resulted in an increase in the S/G ratio in the antisense CCoAOMT plants. This could be explained by the different substrate affinities exhibited by CCoAOMT and CAOMT. In both zinnia and tobacco, CCoAOMT exhibits a higher methylation rate using caffeoyl-CoA than 5-hydroxyferuloyl CoA. Thus, antisense suppression of CCoAOMT may have a more significant effect on guaiacyl lignin production when compared to that of syringyl lignin production. Likewise, CAOMT exhibits a higher methylation rate using 5-hydroxyferulic acid than caffeic acid, which may result in more efficient compensation of syringyl lignin production. The combination of these effects may lead to the differential reduction in guaiacyl lignin and syringyl lignin observed in the antisense CCoAOMT plants. However, CAOMT activity could not compensate for the loss of CCoAOMT to produce normal level of guaiacyl lignin or syringyl lignin.

It was previously demonstrated that antisense suppression of CAOMT activity alone could lead to loss of syringyl lignin production (Tsai et al., Plant Physiol., 117: 101–117 (1998)). CCoAOMT activity does not appear to be able to compensate for the loss of CAOMT to produce syringyl lignin although it could effectively do so to produce normal level of guaiacyl lignin. Because CCoAOMT has been shown herein to participate in the conversion of 5-hydroxyferuloyl CoA to sinapoyl CoA, a reasonable explanation is that the putative ferulyol CoA 5-hydroxylase does not exist in the lignified tissues (FIG. 1). Thus, antisense suppression of CAOMT alone effectively reduces the availability of ferulic acid, which is the only intermediate leading to the methylation of 5-hydroxyl groups catalyzed by CAOMT and CCoAOMT. This results in effective block of syringyl lignin production. In contrast, a reduction in feruloyl CoA caused by the loss of CAOMT could be completely compensated by the CCoAOMT-catalyzed methylation of caffeoyl-CoA, which can be synthesized from either CoA activation of caffeic acid or hydroxylation of p-coumaroyl CoA.

The lignin biosynthesis scheme shown in FIG. 1 places ferulate 5-hydroxylase (F5H) in the only route leading to syringyl lignin production. This is consistent with the results reported in both the mutant lacing F5H and the transgenic plants overexpressing F5H. A mutation in F5H gene in Arabidopsis resulted in complete loss of syringyl lignin production (Chapple et al., *Plant Cell*, 4:1413–1424 (1992)). Furthermore, overexpression of F5H in transgenic Arabidopsis plants led to predominant production of syringyl lignin with little guaiacyl lignin (Meyer et al., *Proc. Natl. Acad. Sci.*, (USA) 95:6619–6623 (1998)).

Although antisense suppression of CAOMT resulted in nearly complete block of syringyl lignin production but no reduction in guaiacyl lignin and lignin content, a decrease in CCoAOMT led to a reduction in lignin content as well as a reduction in both guaiacyl and syringyl lignin monomers. When both CAOMT and CCoAOMT were suppressed in the antisense plants, an additive effect on a reduction in lignin content and an alteration in lignin composition was observed. Simultaneous suppression of both CCoAOMT and CAOMT (TCoA1+9 -TMT-197, TCoA1+9-TMT-215, and TCoA1+9-TMT-251) resulted in a further decrease in lignin content to 34–42% that of the wild type compared to 53–67% that of the wild type seen in the lines (TCoA9-164 and TCoA1+9-123) with antisense suppression of CCoAOMT alone (Table 1). Furthermore, syringyl lignin was further reduced to about 15% that of the wild type in the transgenic lines with the antisense suppression of both CAOMT and CCoAOMT (TCoA1+9-TMT-197, TCoA1+9-TMT-215, TCoA1+9-TMT-251 and TCoA+9-TMT-121), compared to about 60% that of the wild-type observed in the lines with antisense suppression of CCoAOMT alone.

The lignin found in tobacco stems is composed primarily of guaiacyl lignin and syringyl lignin. The presence of hydroxyphenyl lignin is essentially negligible. Thus, although antisense suppression of both CCoAOMT and CAOMT activities blocks the further conversion of caffeic acid and caffeoyl-CoA, this does not appear to result in any increase in hydroxyphenyl lignin content. This finding indicates that the absence of hydroxyphenyl lignin is probably not due to any preferential influx of intermediates toward the guaiacyl and syringyl lignin production. It is most likely due to the lack of reactions leading to the conversion of p-coumaroyl CoA to p-coumaryl alcohol.

As shown in FIG. 4, two to four plants from each group containing the antisense O-methyltransferase (OMT) cassette(s) were selected for assay of CCoAOMT and CAOMT enzyme activities. The OMT activities in the transgenic plants were expressed as a percentage of wild-type activity. Although antisense suppression of CCoAOMT alone or antisense suppression of both CCoAOMT and CAOMT resulted in approximately a 33% to an approximate 66% reduction in lignin content in the resulting transgenic plants, no negative effect on actual plant growth and/or morphology was observed. The transgenic plants appeared to possess normal flowers and seeds, and grow to a similar height as their wild-type counterparts. This supports the proposition that plants can sustain a significant reduction in lignin content without any significant effects on plant growth in greenhouse conditions. The phenotype exhibited by the CCoAOMT antisense transgenic plants appears to be very different from that of plants with suppression of phenylalanine ammonia-lyase (PAL; Elkind et al., *Proc. Natl. Acad. Sci.*, (USA) 87:9057–9061 (1990)) or plants with suppression of cinnamoyl-CoA reductase (CCR; Piquemal et al., *Plant Journal*, 13:71–83 (1998)). However, as phenylalanine ammonia-lyase (PAL) is at an entry point leading to the phenylpropanoid pathway, suppression of PAL blocks biosynthesis of diverse phenolic compounds that may be important for plant growth and survival. Thus, it is expected that abnormal phenotypes are associated with the loss of PAL.

In contrast, antisense suppression of CCoAOMT activity does not affect the biosynthesis of several important compounds, such as flavonoids, chlorogenic acids and salicylic acid, involved in plant defense. Thus, antisense suppression of CCoAOMT activity may be more specific to monolignol biosynthesis. The residual level of monolignols produced in the resulting transgenic plants of the invention, may be sufficient to sustain normal plant growth. However, this could not explain the phenotypic difference between the CCoAOMT antisense plants and the CCR antisense plants (Piquemal et al., *Plant Journal*, 13:71–83 (1998)). For example, in one CCR antisense transgenic line with 47% reduction in the Klason lignin, normal plant growth was dramatically affected. This suggests that factors other than the reduction of lignin content may contribute to the abnormal phenotype observed in CCR antisense plants. In contrast, the CCoAOMT antisense plants having up to 66% lignin reduction when compared to a wild-type plant, grew as normally as the wild-type plant.

Finally, although no visible abnormal phenotype was observed in the resulting CCoAOMT antisense plants, the vessel shapes were significantly altered. This result is similar to the results observed in the CCR antisense tobacco plants (Piquemal et al., *Plant Journal*, 13:71–83 (1998)) as well as in bean plants grown in the presence of an PAL inhibitor, L-$\alpha$-aminooxy-$\beta$-phenylpropionic acid (Amrhein et al., *Eur. J. Cell Bio.*, 29:139–144 (1983); Smart et al., *Protoplasma*, 124:87–95 (1985)). In these cases, a reduction in the lignin content resulted in collapse of xylem vessels. Because the mechanical rigidity of lignin strengthens vessel walls, it is clear that lack of lignin weakens the strength of vessel walls. Weakening of the vessel walls can result in collapse of vessel walls from the negative pressure generated through transpiration. However, it appears that even with some deformed vessels, the transgenic plants of the invention could still transport water and solutes efficiently to support normal growth.

Example 12

Reduction in Lignin Content in Aspen Trees with Antisense Suppression of CCoAOMT The effect of antisense suppression of CCoAOMT on lignin biosynthesis in tree species was investigated in aspen. It was found that antisense suppression of CCoAOMT expression in transgenic aspen trees resulted in a dramatic reduction in lignin content. The reduction in lignin content led to a less condensed and less cross-linked lignin structure in wood. This finding indicates that antisense suppression of CCoAOMT is an efficient means for genetic engineering of trees with low lignin content.

Preparation of Transgenic Aspen Trees

Figure 14:
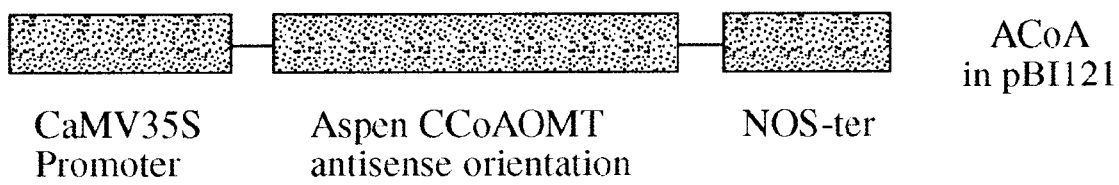
FIG. 14 shows an antisense expression construct of aspen CCoAOMT.

Aspen CCoAOMT cDNA was inserted into the binary vector pBI121 (Clontech) to yield an antisense CCoAOMT expression cassette ACoA. The coding region of the CCoAOMT cDNA was placed in an antisense orientation downstream of the constitutive cauliflower mosaic virus (CaMV) 35S promoter (FIG. 14) and terminated by the polyadenylation signal from the nopline synthase gene (NOS-Ter) of the Agrobacterium Ti plasmid. Aspen stems were transformed with Agrobacteria harboring the binary vector containing the antisense ACoA and used to regenerate plants.

Biochemical Analysis of Plant Materials

Figure 15:
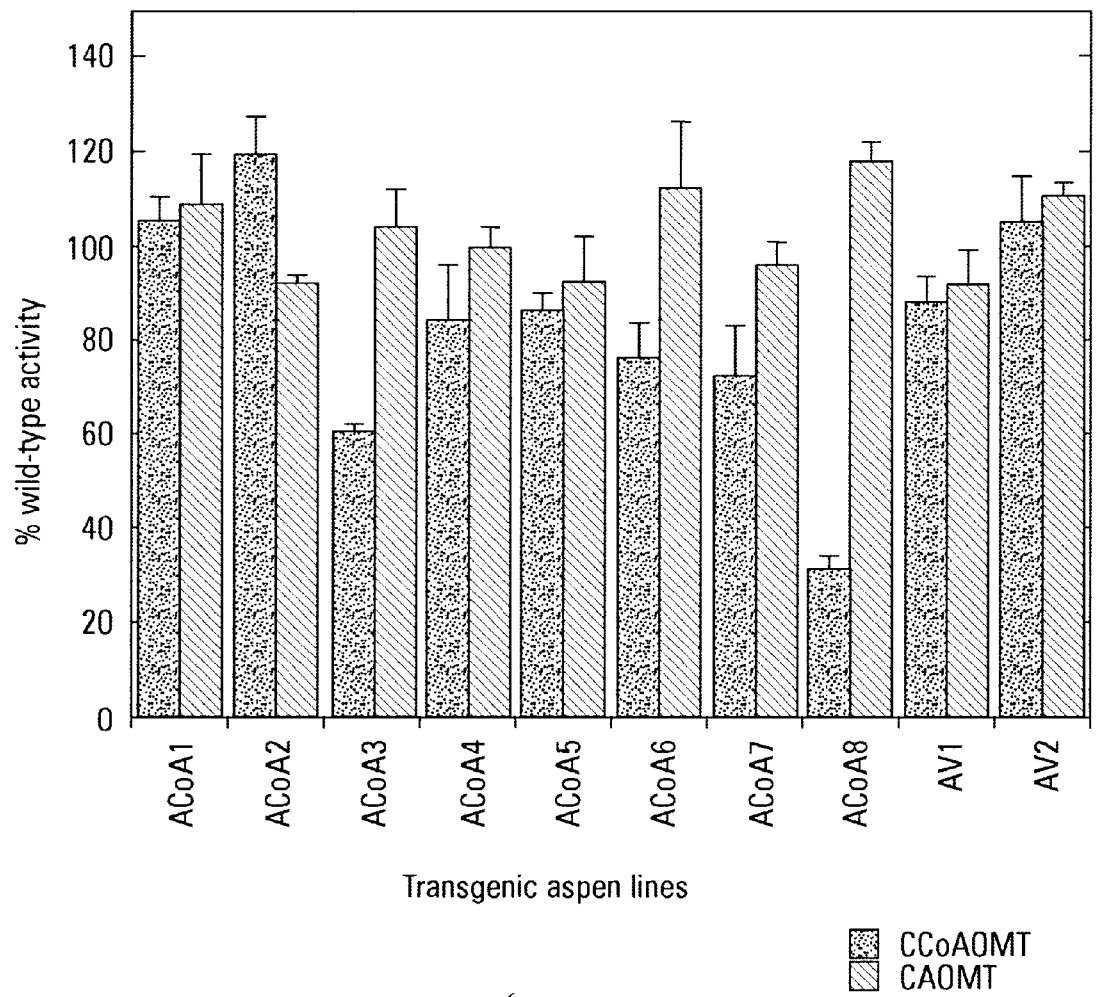
FIG. 15 shows CCoAOMT and CAOMT activities in transgenic aspen plants; ACoA, plants with antisense expression of CCoAOMT; AV, wild type plants transformed with the binary vector pBI121; data are the mean +/–SD of three assays.

CCoAOMT and CAOMT activities were measured in eight transgenic plants, using the methods set forth in Examples 4 and 5. Stems of transgenic plants were used for assay of both activities. O-methyltransferase activities in transgenic plants were expressed as a percentage of wild-type activity. As shown in FIG. 15, the transgenic line ACoA8 had a 70% reduction in CCoAOMT activity. Antisense expression of CCoAOMT did not result in any alteration of CAOMT activity in the transgenic plants, demonstrating that expression of the CCoAOMT antisense cDNA results in a specific reduction in CCoAOMT expression.

Figure 16:
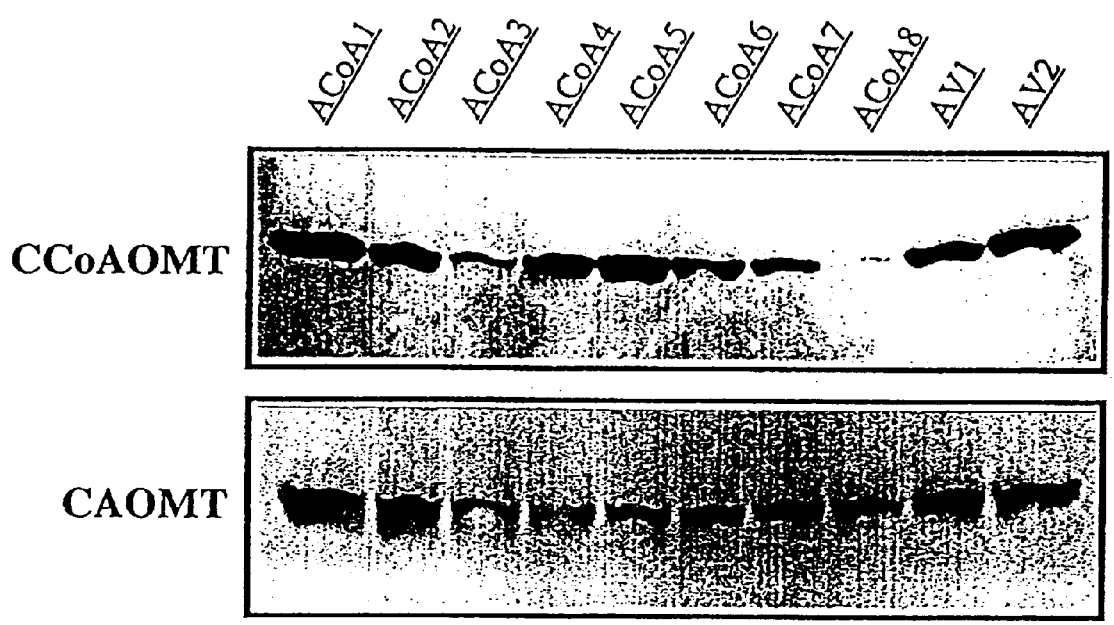
FIG. 16 shows a protein gel blot analysis of CCoAOMT and CAOMT in transgenic aspen plants; figure legend is set forth in FIG. 15.

Reduction in CCoAOMT activity was also detected by protein gel blot analysis (FIG. 16). Ten micrograms of protein extracted from stems of transgenic aspen plants was loaded in each lane. The blot was probed with either antibodies against zinnia CCoAOMT or antibodies against zinnia CAOMT, as described in Example 4. A reduction in CCoAOMT level was evident in the transgenic line ACoA8, which is consistent with the activity assay result.

Figure 17:
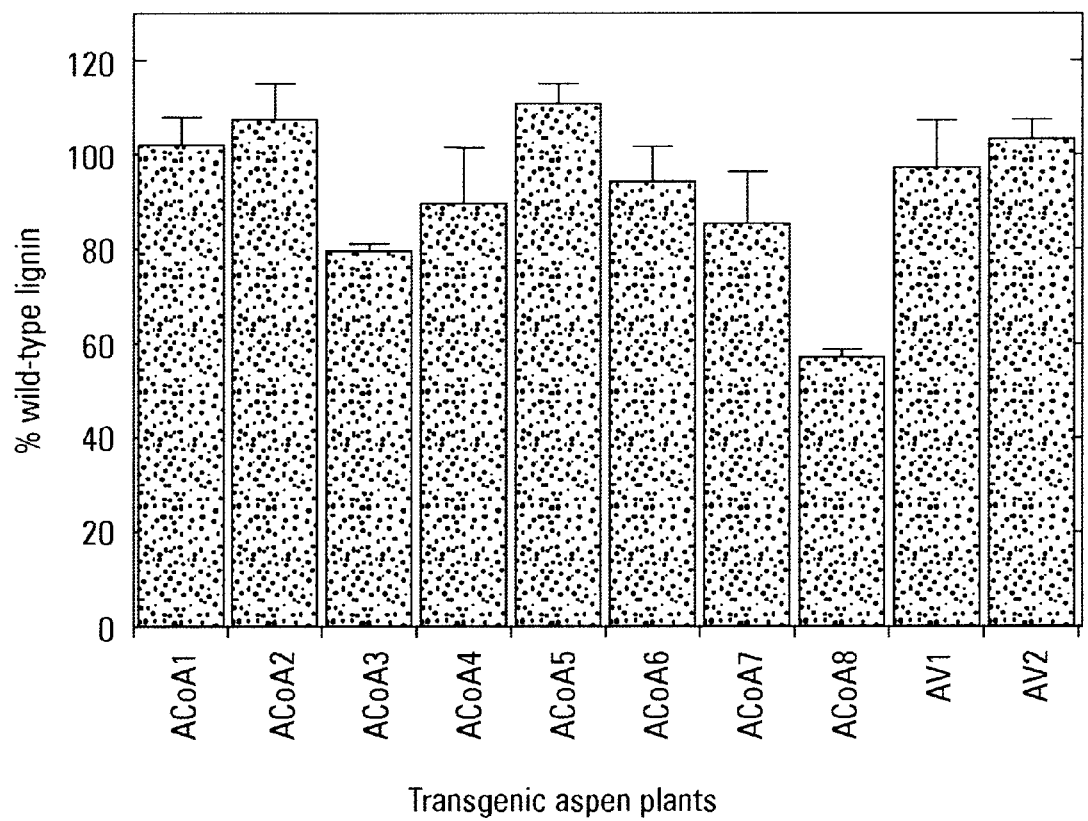
FIG. 17 depicts lignin content in transgenic aspen plants; figure legend is set forth in FIG. 15; data are the mean +/–SD of two assays.

To examine the effects of the reduction in CCoAOMT level on lignin content, stems of transgenic plants were assayed for Klason lignin as in Example 5. Klason lignin in transgenic plants is expressed as a percentage of wild-type lignin. The transgenic line ACoA8 showed a 40% reduction in lignin content (FIG. 17), providing direct evidence that CCoAOMT is essential in lignin biosynthesis during wood formation.

Figure 18:
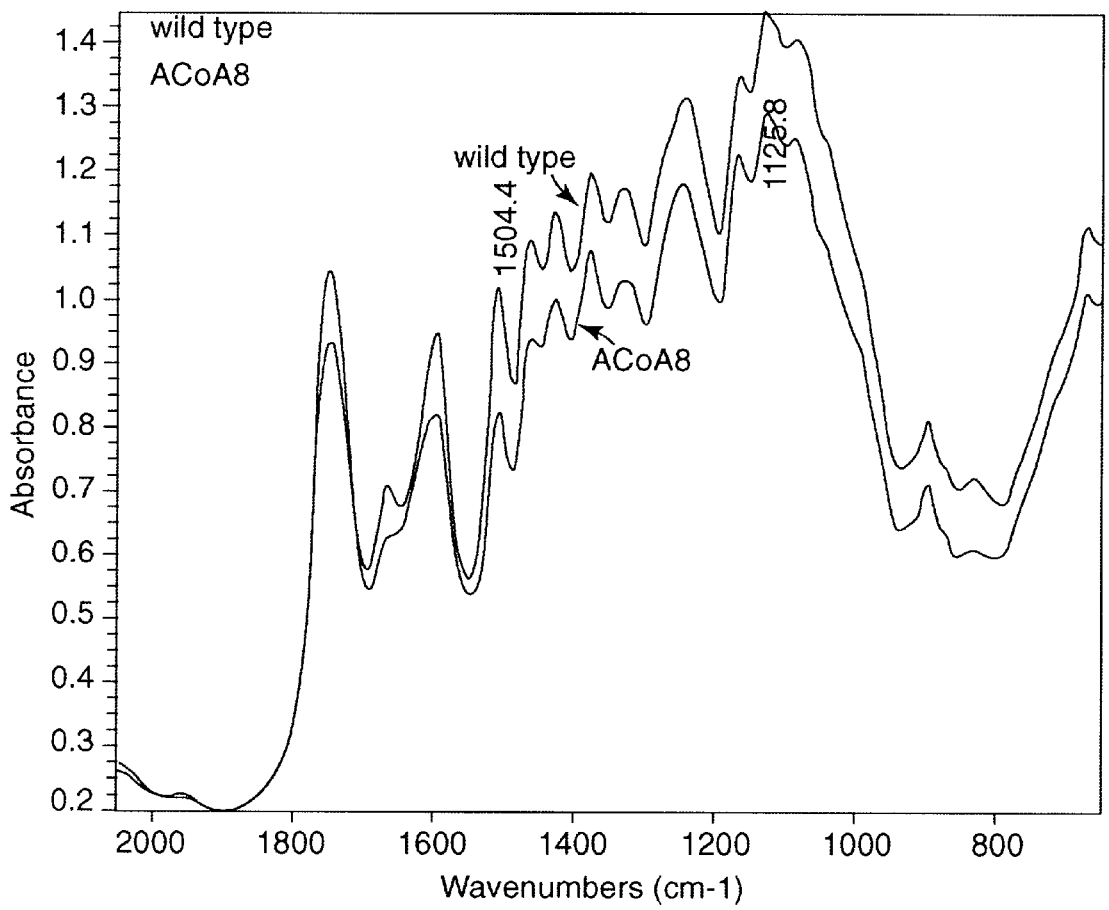
FIG. 18 shows diffuse reflectance infrared Fourier-transform spectra (DRIFTS) of cell walls of the wild-type and transgenic plants; legend is set forth in FIG. 15.

The dramatic reduction in lignin content in transgenic line ACoA8 was also revealed by diffuse reflectance infrared Fourier-transform spectroscopy (DRIFTS). DRIFTS was performed using a Magna system 850 Fourier-transform infrared bench. Lignin absorbances at 1504 $cm^{-1}$ and 1596 $cm^{-1}$, and cellulose absorbance at 1130 $cm^{-1}$ were used for quantitative analysis. Comparison of the DRIFTS spectra of both the wild type and the transgenic line ACoA8 (FIG. 18) showed that in ACoA8, there was a specific reduction in the absorbance at 1504 $cm^{-1}$, the region for lignin absorbance. However, no alteration was observed in the absorbance at 1126 $cm^{-1}$, the region for cellulose absorbance. Quantitative analysis showed that the lignin absorbance at 1504 $cm^{-1}$ was reduced to 68% of the wild type (Table 2). The DRIFTS spectra also provides further evidence that lignin in the transgenic line ACoA8 is less cross-linked. It has been reported that in DRIFTS spectra the absorbances at 1504 $cm^{-1}$ and 1596 $cm^{-1}$ are two absorbances characteristics of lignin, and the absorbance at 1504 $cm^{-1}$ is more intense in condensed, highly cross-linked lignin structure. The higher the 1504:1596 $cm^{-1}$ ratio, the more condensed and cross-linked the lignin structure. Quantitative analysis of the 1504:1596 $cm^{-1}$ ratio between the wild type and the ACoA8 plant (Table 2) clearly showed that the ratio in the ACoA8 plant was reduced to 82% of the wild type. This indicates that the reduction in lignin content in the transgenic line ACoA8 leads to a less condensed and cross-linked lignin structure in wood. This implies that the remaining lignin in the ACoA8 plant should be much easier to be removed than the more condensed and cross-linked lignin in the wild type.

TABLE 2

Quantitative measurement of lignin and cellulose absorbances from the DRIFTS spectra of the wild-type and transgenic plants

| | Absorbances | | | Ratios of Absorbance | |
|---|---|---|---|---|---|
| | lignin (L1) | cellulose (C) | lignin (L2) | | |
| | (1504/cm) | (1130/cm) | (1596/cm) | L1/C | L1/L2 |
| wild type | 0.201 +/− 0.019 | 0.360 +/− 0.017 | 0.266 +/− 0.024 | 0.558 +/− 0.045 | 0.756 +/− 0.014 |
| ACoA8 | 0.133 +/− 0.015 | 0.351 +/− 0.026 | 0.214 +/− 0.016 | 0.379 +/− 0.031 | 0.621 +/− 0.061 |

Each data point is the mean +/−SD of absorbances from five separate DRIFTS spectra.

Notably, although it has 40% reduction in lignin content compared to a wild-type tree, the transgenic aspen tree ACoA8 has been grown normally under the greenhouse conditions. No visible abnormal growth or morphology was observed in the tree.

All patents, patent applications and publications cited herein are incorporated by reference in their entireties as though individually incorporated by reference. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A plant having reduced lignin content compared to the lignin content of a comparable wild-type plant wherein the plant exhibits reduced activity of a caffeoyl-CoA O-methyltransferase (CCoAOMT) compared to the activity of the caffeoyl-CoA O-methyltransferase in the wild plant.

2. The plant of claim 1 which further exhibits reduced activity of a caffeic acid O-methyltransferase (CAOMT).

3. The plant of claim 1 comprising at least one exogenous nucleic acid, wherein the presence in the plant of the at least one exogenous nucleic acid is associated with the reduced CCoAOMT activity.

4. The plant of claim 3 wherein the exogenous nucleic acid is integrated into the genomic DNA of the plant.

5. The plant of claim 3 comprising a first exogenous nucleic acid that is associated with reduced CCoAOMT activity.

6. The plant of claim 5 wherein the first exogenous nucleic acid comprises an "antisense" nucleotide sequence that is "antisense" to at least a portion of a CCoAOMT gene.

7. The plant of claim 6 wherein the "antisense" nucleotide sequence is the complement of at least a portion of a "sense" cDNA sequence selected from the group consisting of SEQ ID NO: 2, SEQ ID NO: 3, SEQ ID NO: 4 and SEQ ID NO: 5.

8. The plant of claim 6 wherein the first exogenous nucleic acid comprises a nucleotide sequence that is complementary to a nucleotide sequence of at least a portion of an endogenous CCoAOMT RNA.

9. The plant of claim 8 wherein the endogenous RNA is a precursor RNA or an mRNA.

10. The plant of claim 5 wherein the first exogenous nucleic acid comprises a "sense" nucleotide sequence that is in a "sense" orientation with respect to at least a portion of a CCoAOMT gene.

11. The plant of claim 5 further comprising a second exogenous nucleic acid that is associated with reduced CAOMT activity.

12. The plant of claim 11 wherein the second exogenous nucleic acid comprises an "antisense" nucleotide sequence that is "antisense" to at least a portion of a CAOMT gene.

13. The plant of claim 12 wherein the "antisense" nucleotide sequence is the complement of at least a portion of the "sense" cDNA sequence SEQ ID NO: 1.

14. The plant of claim 12 wherein the second exogenous nucleic acid comprises a nucleotide sequence that is complementary to a nucleotide sequence of at least a portion of an endogenous CAOMT RNA.

15. The plant of claim 14 wherein the endogenous RNA is a precursor RNA or an mRNA.

16. The plant of claim 11 wherein the second exogenous nucleic acid comprises a "sense" nucleotide sequence that is in a "sense" orientation with respect to at least a portion of a CAOMT gene.

17. The plant of claim 11 wherein the first and second exogenous nucleic acids are present on the same molecule.

18. The plant of claim 1 which is a gymnosperm or an angiosperm.

19. The plant of claim 1 wherein the plant is a forage crop selected from the group consisting of alfalfa, tall fescue and clover.

20. The plant of claim 1 having altered lignin composition compared to the lignin composition of the wild-type plant.

21. The plant of claim 20 having reduced guaiacyl lignin content compared to the guaiacyl lignin content of the wild-type plant.

22. The plant of claim 20 wherein the altered lignin composition is characterized by an increased syringyl lignin/guaiacyl lignin ratio when compared to the syringyl/guaiacyl lignin ratio of the wild-type plant.

23. A plant that exhibits reduced CCoAOMT activity compared to the CCoAOMT activity of a comparable wild-type plant.

24. The plant of claim 23 that further exhibits reduced CAOMT activity compared to the CAOMT activity of a comparable wild-type plant.

25. A genetically engineered plant comprising at least one exogenous nucleic acid comprising a nucleotide sequence that is "antisense" to at least a portion of the CCoAOMT gene, such that the genetically engineered plant exhibits reduced CCoAOMT activity compared to the CCoAOMT activity of a wild-type plant.

26. The genetically engineered plant of claim 25 further comprising at least one exogenous nucleic acid comprising a nucleotide sequence that is "antisense" to at least a portion of the CAOMT gene, such that the genetically engineered plant exhibits reduced CAOMT activity compared to the CAOMT activity of a wild-type plant.

27. A plant having altered lignin composition compared to the lignin composition of a wild-type plant, wherein the plant exhibits reduced activity of a caffeoyl-CoA O-methyltransferase (CCOAOMT) compared to the activity of the caffeoyl-CoA O-methyltransferase in the wild-type plant.

28. The plant of claim 27 which further exhibits reduced activity of a CAOMT.

29. The plant of claim 27 wherein the altered lignin composition of the genetically engineered plant is characterized by an increased syringyl lignin/guaiacyl lignin ratio when compared to the syringyl/guaiacyl lignin ratio of the wild-type plant.

30. A method for making a genetically engineered plant comprising:
   (a) transfecting a plant cell with a first exogenous nucleic acid associated with reduced activity in the plant of a caffeoyl-CoA O-methyltransferase (CCOAOMT) compared to the activity of the caffeoyl-CoA O-methyltransferase in the wild-type plant, to yield a genetically engineered plant cell; and
   (b) growing the genetically engineered plant cell into the genetically engineered plant having reduced lignin content compared to the lignin content of a comparable wild-type plant.

31. The method of claim 30 wherein the first exogenous nucleic acid comprises an "antisense" nucleotide sequence that is "antisense" to at least a portion of a CCoAOMT gene.

32. The method of claim 31 wherein the "antisense" nucleotide sequence is the complement of at least a portion of a cDNA sequence selected from the group consisting of "sense" cDNA sequences SEQ ID NO: 2, SEQ ID NO: 3, SEQ ID NO: 4 and SEQ ID NO: 5.

33. The method of claim 32 wherein the first exogenous nucleic acid comprises a nucleotide sequence that is complementary to a nucleotide sequence of at least a portion of an endogenous CCoAOMT RNA.

34. The method of claim 33 wherein the endogenous RNA is a precursor RNA or an mRNA.

35. The method of claim 30 wherein the first exogenous nucleic acid comprises a "sense" nucleotide sequence that is in a "sense" orientation with respect to at least a portion of a CCoAOMT gene.

36. The method of claim 30 comprising transfecting the plant cell with a second exogenous nucleic acid that is associated with reduced CAOMT activity.

37. The method of claim 36 wherein the second exogenous nucleic acid comprises an "antisense" nucleotide sequence that is "antisense" to at least a portion of a CAOMT gene.

38. The method of claim 37 wherein the "antisense" nucleotide sequence is the complement of at least a portion of the "sense" cDNA sequence SEQ ID NO: 1.

39. The method of claim 37 wherein the second exogenous nucleic acid comprises a nucleotide sequence that is complementary to a nucleotide sequence of at least a portion of an endogenous CAOMT RNA.

40. The method of claim 39 wherein the RNA is a presursor RNA or an mRNA.

41. The method of claim 36 wherein the second exogenous nucleic acid comprises a "sense" nucleotide sequence that is in a "sense" orientation with respect to at least a portion of a CAOMT gene.

42. The method of claim 30 wherein the genetically engineered plant has altered lignin composition compared to the lignin composition of the wild-type plant.

43. The method of claim 42 wherein the altered lignin composition of the genetically engineered plant is characterized by a higher syringyl/guaiacyl ration when compared to the syringyl/guaiacyl ratio of the wild-type plant.

44. The method of claim 30 wherein the genetically engineered plant has reduced guaiacyl lignin content compared to the guaiacyl lignin content of the wild-type plant.

45. The method of claim 30 wherein the genetically engineered plant is a gymnosperm, or an angiosperm.

46. The method of claim 30 wherein the genetically engineered plant is a forage crop selected from the group consisting of alfalfa, tall fescue and clover.

47. A method for making a genetically engineered plant comprising:
   (a) transfecting a plant cell with a vector comprising a first exogenous nucleic acid comprising a first nucleotide sequence that is "antisense" to a CCoAOMT gene to yield a genetically engineered plant cell;
   (b) causing expression of the first exogenous nucleic acid in the genetically engineered plant cell to produce a first "antisense" RNA transcript having a nucleotide sequence that is complementary to a nucleotide sequence of at least a portion of an endogenous CCoAOMT RNA; and
   (c) growing the genetically engineered plant cell into the genetically engineered plant having reduced lignin content compared to the lignin content of a comparable wild-type plant.

48. The method of claim 47 wherein the endogenous CCoAOMT RNA is a precursor RNA or an mRNA.

49. The method of claim 47 wherein the first "antisense" nucleotide sequence is the complement of at least a portion of a cDNA sequence selected from the group consisting of "sense" cDNA sequences SEQ ID NO: 2, SEQ ID NO: 3, SEQ ID NO: 4 and SEQ ID NO: 5.

50. The method of claim 47 wherein the vector further comprises a second exogenous nucleic acid comprising a second nucleotide sequence that is "antisense" to a CAOMT gene, and wherein step (b) further comprises causing expression of the second exogenous nucleic acid in the genetically engineered plant cell to produce a second "antisense" RNA transcript having a nucleotide sequence that is complementary to a nucleotide sequence of at least a portion of an endogenous CAOMT RNA.

51. The method of claim 50 wherein the endogenous CAOMT RNA is a precursor RNA or an mRNA.

52. The method of claim 50 wherein the second "antisense" nucleotide sequence is the complement of at least a portion of the "sense" cDNA sequence SEQ ID NO: 1.

53. A method for making a genetically engineered plant comprising:
   (a) transfecting a plant cell with a first vector comprising a first exogenous nucleic acid comprising a first nucleotide sequence that is "antisense" to a CCoAOMT gene and a second vector comprising a second exogenous nucleic acid comprising a second nucleotide sequence that is "antisense" to a CAOMT gene to yield a genetically engineered plant cell;
   (b) causing expression of the first and second exogenous nucleic acids in the genetically engineered plant cell to produce a first "antisense" RNA transcript having a nucleotide sequence that is complementary to a nucleotide sequence of at least a portion of an endogenous CCoAOMT RNA and a second "antisense" RNA transcript having a nucleotide sequence that is complementary to a nucleotide sequence of at least a portion of an endogenous CAOMT RNA; and (c) growing the genetically engineered plant cell into the genetically engineered plant having reduced lignin content compared to the lignin content of a comparable wild-type plant.

54. The method of claim 53 wherein the endogenous CCoAOMT RNA is a precursor RNA or an mRNA, and wherein the endogenous CAOMT RNA is a precursor RNA or an mRNA.

55. The method of claim 53 wherein the first "antisense" nucleotide sequence is the complement of at least a portion of a cDNA sequence selected from the group consisting of "sense" cDNA sequences SEQ ID NO: 2, SEQ ID NO: 3, SEQ ID NO: 4 and SEQ ID NO: 5.

56. The method of claim 53 wherein the second "antisense" nucleotide sequence is the complement of at least a portion of the "sense" cDNA sequence SEQ ID NO: 1.

57. A method for making a genetically engineered plant comprising:

(a) transfecting a plant cell with at least one exogenous nucleic acid associated with reduced activity in the plant of a caffeoyl-CoA O-methylgransferase (CcoAOMT) compared to the activity of the caffeoyl-CoA O-methyltransferase in the wild-type plant, to yield a genetically engineered plant cell; and (b) growing the genetically engineered plant cell into a genetically engineered plant having reduced lignin content compared to the lignin content of a comparable wild-type plant and altered lignin composition compared to the lignin composition of the comparable wild-type plant.

58. The method of claim 57 wherein the altered lignin composition of the genetically engineered plant is characterized by an increased syringyl lignin/guaiacyl lignin ratio when compared to the syringyl/guaiacyl lignin ratio of the wild-type plant.

* * * * *

UNITED STATES PATENT AND TRADEMARK OFFICE
CERTIFICATE OF CORRECTION

PATENT NO.   : 6,441,272 B1
DATED        : August 27, 2002
INVENTOR(S)  : Zheng-Hua Ze It is certified that error appears in the above-identified patent and that said Letters Patent is hereby corrected as shown below:

<u>Title page,</u>
Item [56], OTHER PUBLICATIONS, after the reference "Van Doorsselaere et al." please insert the reference -- Vignols et al., "The *brown midrib3 (bm3)* Mutation in Maize Occurs in the Gene Encoding Caffeic Acid *O*-Methyltransferase," *Plant Cell*, *8*(6):855-864 (1995). --

<u>Column 12,</u>
Line 16, please delete "ulitlzing" and insert -- utilizing --.

<u>Column 23,</u>
Line 65, please delete "TCoA1+9-TMT-25 1" and insert -- TCoA+9-TMT-251 --.

<u>Column 35,</u>
Line 31, after the word "plant" please insert -- , --.
Line 34, please delete "wild" and insert -- wild-type --.

<u>Column 37,</u>
Lines 12 and 26, please delete "(CCOAOMT)" and insert -- (CCoAOMT) --.
Line 67, please delete "presursor" and insert -- precursor --.

<u>Column 40,</u>
Line 5, please delete "O-methylgransferase" and insert -- O-methyltransferase --.

Signed and Sealed this

Eleventh Day of November, 2003

JAMES E. ROGAN
*Director of the United States Patent and Trademark Office*

SEQUENCE LISTING

<160> NUMBER OF SEQ ID NOS: 13

<210> SEQ ID NO 1
<211> LENGTH: 1507
<212> TYPE: DNA
<213> ORGANISM: Nicotiana tabacum

<400> SEQUENCE: 1

```
gtaaaatggg ttcaacaagc gagagccaga gtaacagtct cactcacaca gaagacgaag     60
ctttcttatt tgccatgcaa ttgtgtagtg cttctgtact tcctatggtc ctaaaatcag    120
```

-continued

```
ccgtagaact tgaccttctt gagctaatgg ctaaggctgg tccaggtgca gctatttctc      180
cttctgaatt agctgctcag ctctcaactc agaacccaga agcacctgtt atgcttgatc      240
ggatgcttag gctacttgct tcttactctg ttctcaattg tactcttaga acactgcctg      300
atagcagtgt tgagaggctt atagtctgct ccccgtctg taagtacttg actaagaatg       360
ctgatggtgt ttctgttgcc ccacttttgc ttatgaatca agataaagtt cttatggaga      420
gctggtacca cttaaaagat gcagtactag atggcggaat cccattcaac aaagcctatg      480
gaatgacagc atttgagtac catggcacag atccaagatt caacaaagtg ttcaaccgtg      540
gaatgtctga tcactccact atgtcaatga agaagattct tgaggactac aaaggatttg      600
aaggcctaaa ttccattgtt gatgttggtg gtggaacggg tgctacagtt aacatgattg      660
tctctaaata tccctctatt aagggcatta actttgattt ccacatgta attggagatg       720 ctccaactta ccccggtgtc gagcacgttg gtggcgacat gtttgctagt gtgccaaaag      780
cagatgccat tttcatgaag tggatttgtc atgattggag cgatgagcat tgcctaaaat      840
tcttgaagaa ttgctatgaa gcactacctg caaatgggaa ggtgataatt gcagagtgca      900
tacttccaga ggccccagat acatcacttg caactaagaa tacagtacat gttgatattg      960
tgatgttagc ataaaccca ggaggcaaag aaaggactga aaggaatttt gaggctttgg      1020
ctaagggcgc tggttttact ggtttcgcaa ggcttgttgc gcttacaaca cttgggtcat      1080
ggaattcaac aagtaattaa tcgattcctt aattcgaagg attaagcaat atactgttcg      1140
ttttgcattt ggaaattcta cttttctcag agtggcttga ctgtgaaaaa aaaaaaaaa      1200 cgacagcaac ggaattccgt tgctgtcgat ctgcagcaag ctctctttac gagtaccctc      1260
gtcaacctca gtatcgatat tagtttccaa taaaggtact accatcacat ggggctctgt      1320
taattgttac catcagaatt acgcagccta aaacttgtga ttgtagtttg agctgtattc      1380
cgtgttattc ctcaattctc tccctaagca agatattagc agatgataaa aaaaaaaaa       1440 aaaaaaaaaa aaaaaaaaaa aaaaaaaaaa aaaaaaaaaa aaaaaaaaaa aaaaaaaaaa     1500
aaaaaaa                                                              1507
```

<210> SEQ ID NO 2
<211> LENGTH: 870
<212> TYPE: DNA
<213> ORGANISM: Nicotiana tabacum

<400> SEQUENCE: 2

```
atggcagaga acggaattaa acaccaagag gttggccaca aaagcctttt gcaaagtgat       60
gctctttacc agtacatact tgaaaccagt gtatacccaa gagagccaga atccatgaaa      120
gagctcaggg aggtgactgc taagcatcca tggaatttaa tgacaacatc agcggatgaa      180
gggcagtttt tgaacatgtt gttgaagttg atcaatgcca aaaacacaat ggagattgga      240
gtttacactg gctactccct ccttgctact gcccttgcta tccccgatga tggaaagata      300
ttggcaatgg acattaacag ggaaaattac gaaataggat tgcccataat cgaaaaggcc      360
ggtgtggctc acaaaattga atttagagaa ggccctgctt tgcccgttct tgatcaactg      420
gttgaagata aaaagaatca tggcacgtat gatttcatat ttgtggatgc tgataaggac      480
aactacatta actatcacaa aaggataata gatttggtga agttggtgg tttaattggg      540 tacgacaaca cccatggaa tggttctgtg gtggctccac ctgatgcacc aatgaggaaa      600
tacgtaaggt attataggga cttcgtgttg gaacttaaca agcccctagc cgttgatcca      660
```

-continued

```
aggattgaga tttgcatgct acccgttggt gatggcatta ccttgtgccg ccgcatcacc    720
tgatcattcc aatattcttt tgtttctttt tatttctaaa tatataaaat aaaaaaaaca    780
ttttctttct tgtttctctt tttggtttat aatgtaaggg aggacttcct tttaagctat    840
gagtttcata ttttcaaaa aaaaaaaaaa                                      870
```

<210> SEQ ID NO 3
<211> LENGTH: 811
<212> TYPE: DNA
<213> ORGANISM: Nicotiana tabacum

<400> SEQUENCE: 3

```
gacgctcttt accagtacat acttgaaacc agtgtatacc aagagagcc agaatccatg     60 aaagagctta gggaggtgac tgctaagcat ccatggaatt taatgacaac atcagcggat   120
gaaggacagt tcttgaacat gttgttgaag ttgattaatg ctaaaaatac aatggagatt   180
ggagtttaca ctggctactc cctccttgct actgcccttg ctatccccga tgatggaaag   240
atattagcaa tggacattaa cagggaaaat tacgaaatag gattgcccat aatagaaaag   300
gccggtgtgg ctcacaaaat tgaatttaga gaaggccctg ctttgcctgt tcttgatcaa   360
ttggttgaag ataaaaagaa tcatggcaca tatgatttca tatttgtgga tgctgacaag   420
gacaactaca ttaactatca caaaaggata atagatttgg tgaaagttgg tggtttgatt   480
gggtacgaca cacccctatg gaatggttct gtggtggctc cacccgatgc accaatgagg   540
aaatacgtaa ggtattacag ggactttgta ttggagctta caaagcccct agccgttgat   600
cctaggattg agatttgtat gttacctgtt ggtgatggca ttaccttgtg ccgccgcatc   660
agctgatcat tccaatattc ttttgtttct tttttatttc taagtataaa aaaaaaaacc   720 ttttctttt tgtttctctt tggtttata atgtaaggga ggacttcctt ttgagctatg    780
agtatcatat tattcaataa aaaaaaaaa a                                   811
```

<210> SEQ ID NO 4
<211> LENGTH: 845
<212> TYPE: DNA
<213> ORGANISM: Nicotiana tabacum

<400> SEQUENCE: 4

```
gcacaggaaa atcaggtcgc caaacaccaa gaggttggcc acaagagcct tttacaaagt    60
gatgctcttt accagtacat acttgagacc agcgtatacc aagagagcc agaacccatg   120 aaagagctca gagaattgac tgctaagcat ccatggaatc taatgacaac ttcggcggat   180
gaaggacaat tcttgatcat gctattgaaa ttgatcaatg ctaaaaacac catggaaatc   240
ggtgtttaca ctggctactc cctccttgct actgctcttg ctcttcccca tgatggaaag   300
atattggcaa tggatattaa cagggaaaat tacgaaatcg ggttgcccgt aatccaaaag   360
gctggcgtgg ctcacaagat tgattttcga gaaggtcctg ctttacctgt tcttgattta   420
atggttgaag ataaaaataa tcatggcacg tatgatttca ttttcgtgga tgctgacaag   480
gacaattaca tcaactacca agaggata atagaattag tgaaagttgg tggtgtgatt   540
ggctacgaca cacccctatg gaatggttct gtggcagctc cacctgatgc ccctatgagg   600
aaatacgtaa ggtactatag ggatttcgta ttggaactta caaagcatt ggcagctgat   660 ccaagaattg agatttgcat gcttcccgtt ggagatggaa ttaccctgtg ccgccgcatc   720
agctgatttt ttttttatcca actacctttg ttttctttt gatttgtgaa taaatatttt   780
gtatctcatg actattatcg ctattaatat ttctatatat ttgtatttca aaaaaaaaa   840
```

```
aaaaa                                                            845

<210> SEQ ID NO 5
<211> LENGTH: 967
<212> TYPE: DNA
<213> ORGANISM: Nicotiana tabacum

<400> SEQUENCE: 5
atggctgaga acggtgcagc acaggaaaat caggttacca aacaccaaga ggttggccac     60
aagagccttt tgcaaagtga tgctctttac cagtacatac ttgagaccag cgtataccca    120
agagagccag aacccatgaa agagctcaga gaattgactg ctaagcatcc atggaatcta    180
atgacaactt cggcggatga aggacaattc ttgagcatgc tattgaagct gatcaatgct    240
aaaaatacaa tggaaattgg tgtttacact ggctactccc ttcttgcaac tgctcttgct    300
cttcctgatg atggaaagat attggcaatg gatattaaca aggaaaatta cgaactcggg    360
ttgcccgtaa tccaaaaggc tggcgtggct cataaaattg attttagaga aggtcctgct    420
ttgcctgttc ttgatttaat gattgaagat aaaaataatc atggcacata tgatttcatt    480
ttcgtggatg ctgacaagga caattacatc aactaccaca agagaataat agaattagtg    540
aaagttggtg gtgtgattgg ctacgacaac accctatgga atggttctgt ggtggctcca    600
cctgatgctc caatgaggaa atacgtaagg tactataggg acttcgtatt ggaacttaac    660
aaagctttgg cagctgatcc aagaattgag atttgcatgc ttcccgttgg tgatggaatt    720
accctgtgcc gccgcatcag ctgatttatt ctgtttatcc aactactttt gtttttcttt    780
tgatttgtga ataaatattt tgtatctcat gattatcgct attaatattt ctatatattt    840
gtatttcaaa tattgtacta ctgaaattgt aacaaatact taagattgta ctacagaaat    900
gattatcgct cgagtaaagt ttatttacaa aatgatattt tatcctttgt aaaaaaaaaa    960
aaaaaaa                                                              967

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 8
ttgcttgata tcatggctga gaacggtgca gcac                                 34

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 9
ttgcttacta gtcagtgctg atgcggcggc aca                                  33

<210> SEQ ID NO 10
<211> LENGTH: 34
<212> TYPE: DNA
<213> ORGANISM: Nicotiana tabacum

<400> SEQUENCE: 10
ttgcttgata tcatggcaga gaacggaatt aaac                                 34
```

```
<210> SEQ ID NO 11
<211> LENGTH: 33
<212> TYPE: DNA
<213> ORGANISM: Nicotiana tabacum

<400> SEQUENCE: 11
ttgcttacta gtcagtgctg atgcggcggc aca                           33

<210> SEQ ID NO 12
<211> LENGTH: 20
<212> TYPE: DNA
<213> ORGANISM: Nicotiana tabacum

<400> SEQUENCE: 12
ccttcgcaag acccttcctc                                          20

<210> SEQ ID NO 13
<211> LENGTH: 24
<212> TYPE: DNA
<213> ORGANISM: Nicotiana tabacum

<400> SEQUENCE: 13
gcctatggaa tgacagcatt tgag                                     24
```